US007901883B2

(12) United States Patent
Poetter et al.

(10) Patent No.: US 7,901,883 B2
(45) Date of Patent: Mar. 8, 2011

(54) HUMAN PAPILLOMA VIRUS (HPV) DETECTION USING NUCLEIC ACID PROBES, MICROBEADS AND FLUORESCENT-ACTIVATED CELL SORTER (FACS)

(75) Inventors: Karl Poetter, Northcote (AU); Toby Gould, Brunswick (AU)

(73) Assignee: Genera Biosystems Limited, Scoresby, Victoria (AU)

(*) Notice: Subject to any disclaimer, the term of this patent is extended or adjusted under 35 U.S.C. 154(b) by 214 days.

(21) Appl. No.: 11/721,429

(22) PCT Filed: Dec. 9, 2005

(86) PCT No.: PCT/AU2005/001865
§ 371 (c)(1),
(2), (4) Date: Aug. 2, 2007

(87) PCT Pub. No.: WO2006/060872
PCT Pub. Date: Jun. 15, 2006

(65) Prior Publication Data
US 2010/0015594 A1    Jan. 21, 2010

Related U.S. Application Data

(60) Provisional application No. 60/704,974, filed on Aug. 3, 2005.

(30) Foreign Application Priority Data

Dec. 10, 2004  (AU) ............................... 2004907070

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| 4,983,728 | A | | 1/1991 | Herzog et al. |
| 5,346,811 | A | | 9/1994 | Galindo-Castro et al. |
| 5,364,758 | A | | 11/1994 | Meijer et al. |
| 5,411,857 | A | | 5/1995 | Beaudenon et al. |
| 5,484,699 | A | | 1/1996 | Bouma et al. |
| 5,527,898 | A | | 6/1996 | Bauer et al. |
| 5,580,970 | A | | 12/1996 | Hendricks et al. |
| 5,643,715 | A | | 7/1997 | Lancaster |
| 5,656,423 | A | | 8/1997 | Orth et al. |
| 5,705,627 | A | | 1/1998 | Manos et al. |
| 5,712,092 | A | | 1/1998 | Orth et al. |
| 5,876,922 | A | | 3/1999 | Orth et al. |
| 5,958,674 | A | | 9/1999 | Beaudenon et al. |
| 5,981,171 | A | | 11/1999 | Kuhns |
| 5,981,180 | A | * | 11/1999 | Chandler et al. .................. 435/6 |
| 6,265,154 | B1 | | 7/2001 | Kroeger et al. |
| 6,312,928 | B1 | | 11/2001 | Van Gemen et al. |
| 6,352,825 | B1 | * | 3/2002 | Meijer et al. ....................... 435/5 |
| 6,482,588 | B1 | | 11/2002 | Van Doorn et al. |
| 6,511,805 | B1 | | 1/2003 | Gocke et al. |
| 6,583,278 | B1 | | 6/2003 | Carter |
| 7,063,963 | B2 | | 6/2006 | Cole et al. |
| 7,183,053 | B2 | | 2/2007 | Gocke et al. |
| 2002/0081617 | A1 | * | 6/2002 | Buranda et al. .................... 435/6 |
| 2003/0224385 | A1 | * | 12/2003 | Pihan ................................. 435/6 |

FOREIGN PATENT DOCUMENTS

| WO | WO 97/14028 A2 | | 4/1997 |
| WO | WO 02/24959 | * | 3/2002 |
| WO | WO 02/40698 A2 | | 5/2002 |
| WO | WO 03/019143 | | 3/2003 |
| WO | WO 2004/018500 A1 | | 3/2004 |
| WO | WO 2005/003380 A1 | | 1/2005 |

OTHER PUBLICATIONS

Baldwin et al., "Human papillomavirus infection in men attending a sexually transmitted disease clinic," Journal of Infectious Diseases, 2003, vol. 187, pp. 1064-1070.
Bleeker et al., "Concordance of specific human papillomavirus types in sex partners is more prevalent than would be expected by chance and is associated with increased viral loads," Clinical Infectious Diseases, 2005, vol. 41, pp. 612-620.
Bosch et al., "The aetiology of cervical cancer," NHSCSP Publication No. 22, Sep. 2005, pp. 1-80.
Brown et al., "Distribution of human papillomavirus types in cervicovaginal washings from women evaluated in a sexually transmitted disease clinic," Sexually Transmitted Diseases, Dec. 2002, pp. 763-768.
Cavuslu et al., "Analytic sensitivities of hybrid-capture, consensus and type-specific polymerase chain reactions for the detection of human papillomavirus type 16 DNA," Journal of Medical Virology, 1996, vol. 49, pp. 319-324.
Evans et al., "Touchdown general primer (GP5+/GP6+) PCR and optimized sample DNA concentration support the sensitive detection of human papillomavirus," BMC Clinical Pathology, 2005, vol. 10:5, pp. 1-14.
Gravitt et al., "Improved amplification of genital human papillomaviruses," Journal of Clinical Microbiology, Jan. 2000, vol. 38, No. 1, pp. 357-361.
Gravitt et al., "A comparison between real-time polymerase chain reaction and hybrid capture 2 for human papillomavirus DNA quantitation," Cancer Epidemiology, Biomarkers & Prevention, Jun. 2003, vol. 12, pp. 477-484.
Hart et al., "Novel method for detection, typing, and quantification of human papillomaviruses in clinical samples," Journal of Clinical Microbiology, Sep. 2001, vol. 39, No. 9, pp. 3204-3212.
Jacobs et al., "A quantitative polymerase chain reaction-enzyme immunoassay for accurate measurements of human papillomavirus type 16 DNA levels in cervical scrapings," British Journal of Cancer, 1999, vol. 81(1), pp. 114-121.
Jastania et al., "Characteristics of Apparently False-Negative Digene Hybrid Capture 2 High-Risk HPV DNA Testing," American Journal of Clinical Pathology, 2006, vol. 125(2), pp. 223-228.

(Continued)

*Primary Examiner* — Juliet C Switzer
(74) *Attorney, Agent, or Firm* — Knobbe Martens Olson & Bear LLP

(57) ABSTRACT

The present invention relates generally to the field of diagnostic and detection assays. More particularly, the present invention provides methods, and reagents including biochips for detecting the presence of, or distinguishing between, one or more analytes in a sample.

15 Claims, 16 Drawing Sheets

OTHER PUBLICATIONS

Lai et al., "Differential viral loads of human papillomavirus 16 and 58 infections in the spectrum of cervical carcinogenesis," International Journal of Gynecological Cancer, 2006, vol. 16, pp. 730-735.

Lapin et al., "Oncologic colpocytology collected in the public health and reference services in the diagnostic of the severity of intraepithelial cervical lesion," Journal of Public Health, Apr. 2000, vol. 34, No. 2, pp. 120-125.

Lorincz et al., "Viral load of human papillomavirus and risk of CIN3 or cervical cancer," The Lancet, Jul. 20, 2002, vol. 360, pp. 228-229.

McQueen et al., "Using a quality control approach to define an 'adequately cellular' liquid-based cervical cytology specimen," Cytopathology, Aug. 2006, vol. 17, issue 4, pp. 168-174.

Minkoff et al., "The effect of highly active antiretroviral therapy on cervical cytologic changes associated with oncogenic HPV among HIV-infected women," AIDS 2001, vol. 15, No. 16, pp. 2157-2164.

Quint et al., "Results of the first World Health Organization international collaborative study of detection of human papillomavirus DNA," Journal of Clinical Microbiology, Feb. 2006, vol. 44, No. 2, pp. 571-579.

Ruffin et al., "Low-dose topical delivery of all-trans retinoic acid for cervical intraepithelial neoplasia II and III," Cancer Epidemiology, Biomarkers & Prevention, Dec. 2004, vol. 13(12), pp. 2148-2152.

Sherman et al., "Determinants of human papillomavirus load among women with histological cervical intraepithelial neoplasia 3: dominant impact of surrounding low-grade lesions," Cancer Epidemiology, Biomarkers & Prevention, Oct. 2003, vol. 12, pp. 1038-1044.

Stevens et al., "Assessment of MagNA pure LC extraction system for detection of human papillomavirus (HPV) DNA in PreservCyt samples by the Roche Amplicor and Linear Array HPV tests," Journal of Clinical Microbiology, Jul. 2006, vol. 44, No. 7, pp. 2428-2435.

Swan et al., "A sensitive, type-specific, fluorogenic probe assay for detection of human papillomavirus DNA," Journal of Clinical Microbiology, Apr. 1997, vol. 35, No. 4, pp. 885-891.

Swan et al., "Human papillomavirus (HPV) DNA copy number is dependant on grade of cervical disease and HPV type," Journal of Clinical Microbiology, Apr. 1999, vol. 37, No. 4, pp. 1030-1034.

Tapsall et al., "Applications of molecular testing in clinical laboratories for the diagnosis and control of gonorrhea," Future Microbiology, 2006, vol. 1(3), pp. 1-7.

Tsai et al., "Association between quantitative high-risk human papillomavirus DNA load and cervical intraepithelial neoplasm risk," Cancer Epidemiology, Biomarkers & Prevention, Nov. 2005, vol. 14(11), pp. 2544-2549.

Van Duin et al., "Human papillomavirus 16 load in normal and abnormal cervical scrapes: An indicator of CIN II/III and viral clearance," International Journal of Cancer, 2002, vol. 98, pp. 590-595.

Venturoli et al., "Evaluation of immunoassays for the detection and typing of PCR amplified human papillomavirus DNA," Journal of Clinical Pathology, 1998, vol. 51, pp. 143-148.

Wallboomers et al., "Human papillomavirus is a necessary cause of invasive cervical cancer worldwide," Journal of Pathology, 1999, vol. 189, pp. 12-19.

Weissenborn et al., "Oncogenic human papillomavirus DNA loads in human immunodeficiency virus-positive women with high-grade cervical lesions are strongly elevated," Journal of Clinical Microbiology, Jun. 2003, vol. 41, No. 6, pp. 2763-2767.

Ylitalo et al., "Consistent high viral load of human papillomavirus 16 and risk of cervical carcinoma in situ: a nested case-control study," The Lancet, Jun. 24, 2000, vol. 355, pp. 2194-2198.

Zerbini et al., "Distribution and viral load of type specific HPVs in different cervical lesions as detected by PCR-ELISA," Journal of Clinical Pathology, 2001, vol. 54, pp. 377-380.

Defoort, J-P et al. 2000 "Simultaneous detection of multiplex-amplified Human Immunodeficiency Virus Type 1 RNA, Hepatitis C Virus RNA, and Hepatitus B Virus DNA using a flow cytometer microsphere-based hybridization assay" *J Clin Microbiol* 38:1066-1071.

Spiro, A. et al. 2000 "A bead-based method for multiplexed identification and quantitation of DNA sequences using flow cytometry" *Applied and Environmental Microbiol* 66:4258-4265.

* cited by examiner

FIGURE 7

| Strain | Bead size | TMR labeling |
|---|---|---|
| 6 | 3.0um | 100% |
| 11 | 3.0um | 0% |
| 16 | 5.0um | 20% |
| 18 | 5.0um | 100% |
| 31 | 4.1um | 0% |
| 33 | 5.0um | 0% |
| 35 | 5.6um | 0% |
| 39 | 3.5um | 100% |
| 45 | 3.5um | 20% |
| 51 | 4.1um | 20% |
| 52 | 6.8um | 20% |
| 56 | 4.1um | 100% |
| 58 | 6.8um | 20% |
| 59 | 5.6um | 20% |
| 68 | 6.8um | 100% |
| HPV control | 5.6um | 100% |
| LC1 control | 3.5um | 0% |

FIGURE 9

| | | | |
|---|---|---|---|
| Probe 6 | /5Acryd/iAmMC6T/AATTAACCCTCACT | AAAGGGAGGACAGCTATGGAC | ATCCGTAACTACATCTTCCACATACACCAA (SEQ ID NO:5) |
| Probe 11 | /5Acryd/AATGGAATTAACCCTCACT | AAAGGGAGGACAGCTATGGAC | ATCTGTGTCTAAATCGCTACATACACTAA (SEQ ID NO:6) |
| Probe 31 | /5Acryd/AATGGAATTAACCCTCACT | AAAGGGAGGACAGCTATGGAC | TGTTTTGTGCTGCAATTGCAAACAGTGATAC (SEQ ID NO:7) |
| Probe 33 | /5Acryd/AATGGAATTAACCCTCACT | AAAGGGAGGACAGCTATGGAC | TTTATGCACACAAGTAACTAGTGACAGTAC (SEQ ID NO:8) |
| Probe 35 | /5Acryd/AATGGAATTAACCCTCACT | AAAGGGAGGACAGCTATGGAC | GTCTGTGTGTTCTGCTGTGTCTTCTAGTGA (SEQ ID NO:9) |
| Probe 39 | /5Acryd/AATGG/iAmMC6T/AATTAACCCTCACT | AAAGGGAGGACAGCTATGGAC | TCTACCTCTATAGAGTCTTCCATACCTTCT (SEQ ID NO:10) |
| Probe 45 | /5Acryd/AATGG/iAmMC6T/AATTAACCCTCACT | AAAGGGAGGACAGCTATGGAC | ACACAAAATCCTGTGCCAAGTACATATGAC (SEQ ID NO:11) |
| Probe 51 | /5Acryd/AATGG/iAmMC6T/AATTAACCCTCACT | AAAGGGAGGACAGCTATGGAC | AGCACTGCCACTGCTGCGGTTTCCCAACA (SEQ ID NO:12) |
| Probe 52 | /5Acryd/AATGG/iAmMC6T/AATTAACCCTCACT | AAAGGGAGGACAGCTATGGAC | TGCTGAGGTTAAAAGGAAAGCACATATAA (SEQ ID NO:13) |
| Probe 56 | /5Acryd/AATGG/iAmMC6T/AATTAACCCTCACT | AAAGGGAGGACAGCTATGGAC | GTACTGCTACAGAACAGTTAAGGAAGGTAC (SEQ ID NO:14) |
| Probe 58 | /5Acryd/AATGG/iAmMC6T/AATTAACCCTCACT | AAAGGGAGGACAGCTATGGAC | ATTATGCACTGAAGTAACTAAGGAAGTAC (SEQ ID NO:15) |
| Probe 59 | /5Acryd/AATGG/iAmMC6T/AATTAACCCTCACT | AAAGGGAGGACAGCTATGGAC | TCTACTACTTCTTCTATTCCTAATGTATAC (SEQ ID NO:16) |
| Probe 68 | /5Acryd/AATGG/iAmMC6T/AATTAACCCTCACT | AAAGGGAGGACAGCTATGGAC | TCTACTACTACTGAATCAGCTGTACCAAAT (SEQ ID NO:17) |
| Probe 16 | /5Acryd/AATGG/iAmMC6T/AATTAACCCTCACT | AAAGGGAGGACAGCTATGGAC | GTCATTATGTGCTGCCATATCTACTTCAGA (SEQ ID NO:18) |
| Probe 18 | /5Acryd/AATGG/iAmMC6T/AATTAACCCTCACT | AAAGGGAGGACAGCTATGGAC | TGCTTTCTACACAGTCTCCTGTACCTGGCA (SEQ ID NO:19) |
| Probe 66 | /5Acryd/AATGG/iAmMC6T/ | AAAGGGAGGACAGCTATGGAC | TATTAATGCAGTCAAAGCACATTAACTAA (SEQ ID NO:20) |
| MlC1_Ac | /5Acryd/ | AAAGGGAGGACAGCTATGGAC | CAAACACAGACACAGAGACCCACAGACA (SEQ ID NO:21) |
| GP5+_For_Ac | /5Acryd/AATGG/iAmMC6T/AATTAACCCTCACT | AAAGGGAGGACAGCTATGGAC | TTTGTTACTGTGGTAGATACTAC (SEQ ID NO:22) |

| | | |
|---|---|---|
| MlC1_reg_FP | /5Phos/TACACACAGGTGTACACAGA | (SEQ ID NO:23) |
| MlC1_reg_R | /5AmMC6/ACCAAGTACTTCTACGTGTTG | (SEQ ID NO:24) |

| | | |
|---|---|---|
| GP5d+ | /5Phos/TTTKTTACHGTKGTDGATACYAC | (SEQ ID NO:25) |
| GP6d+ | /5AmMC6/GAAAHATAAAYTGYAADTCATAYTC | (SEQ ID NO:26) |

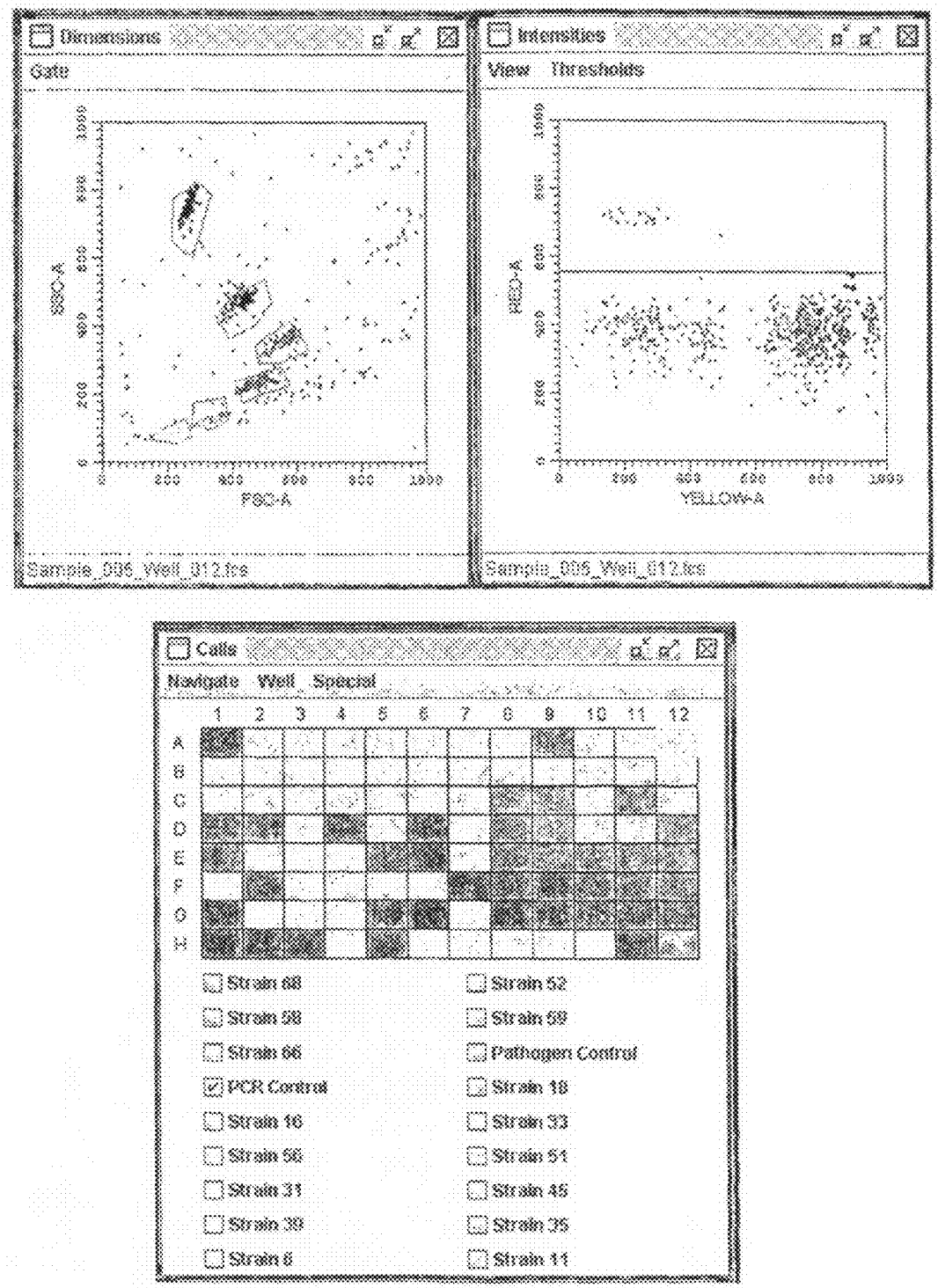
FIGURE 10A - Human PCR control only

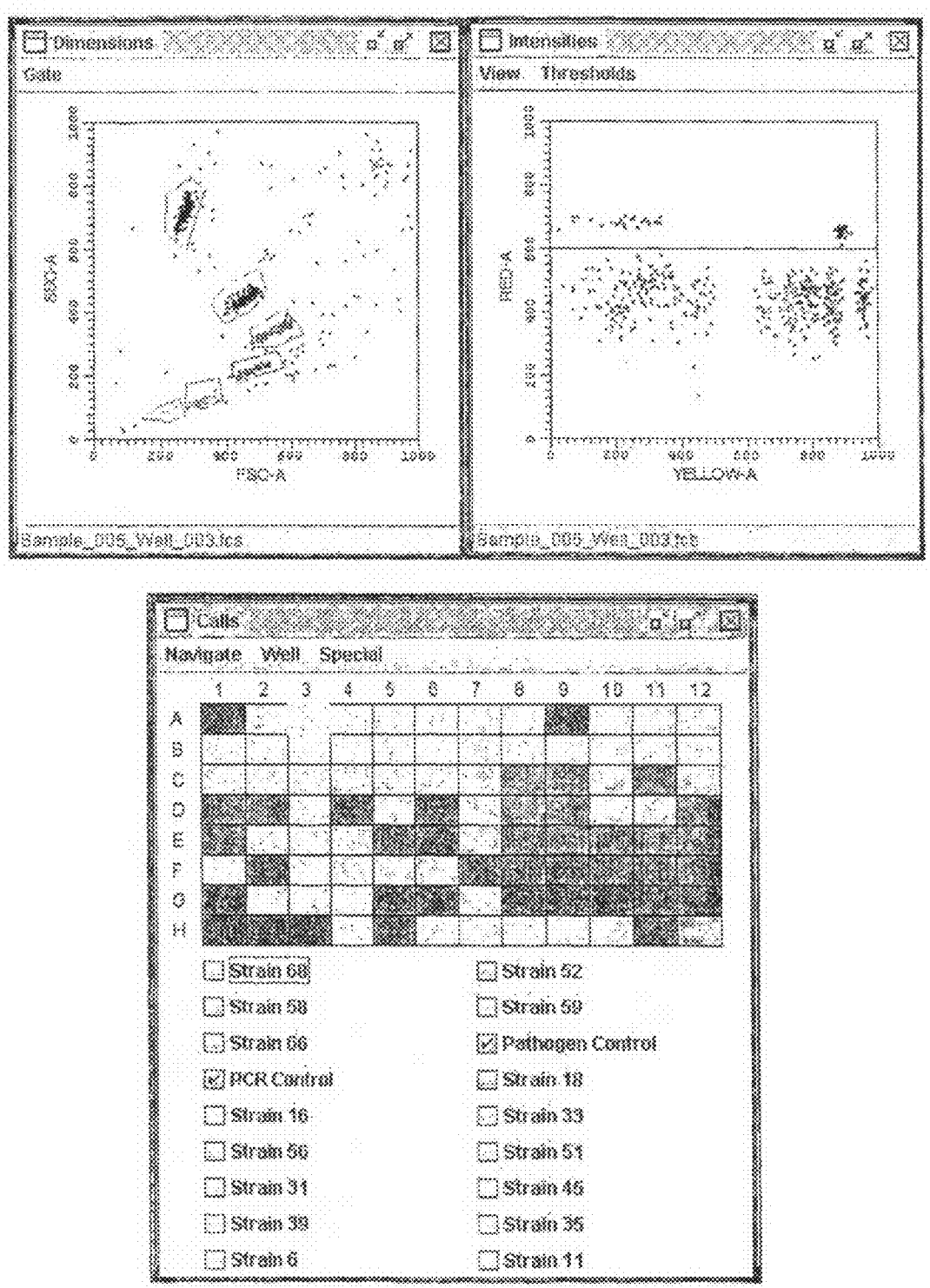
FIGURE 10B - Human + HPV control

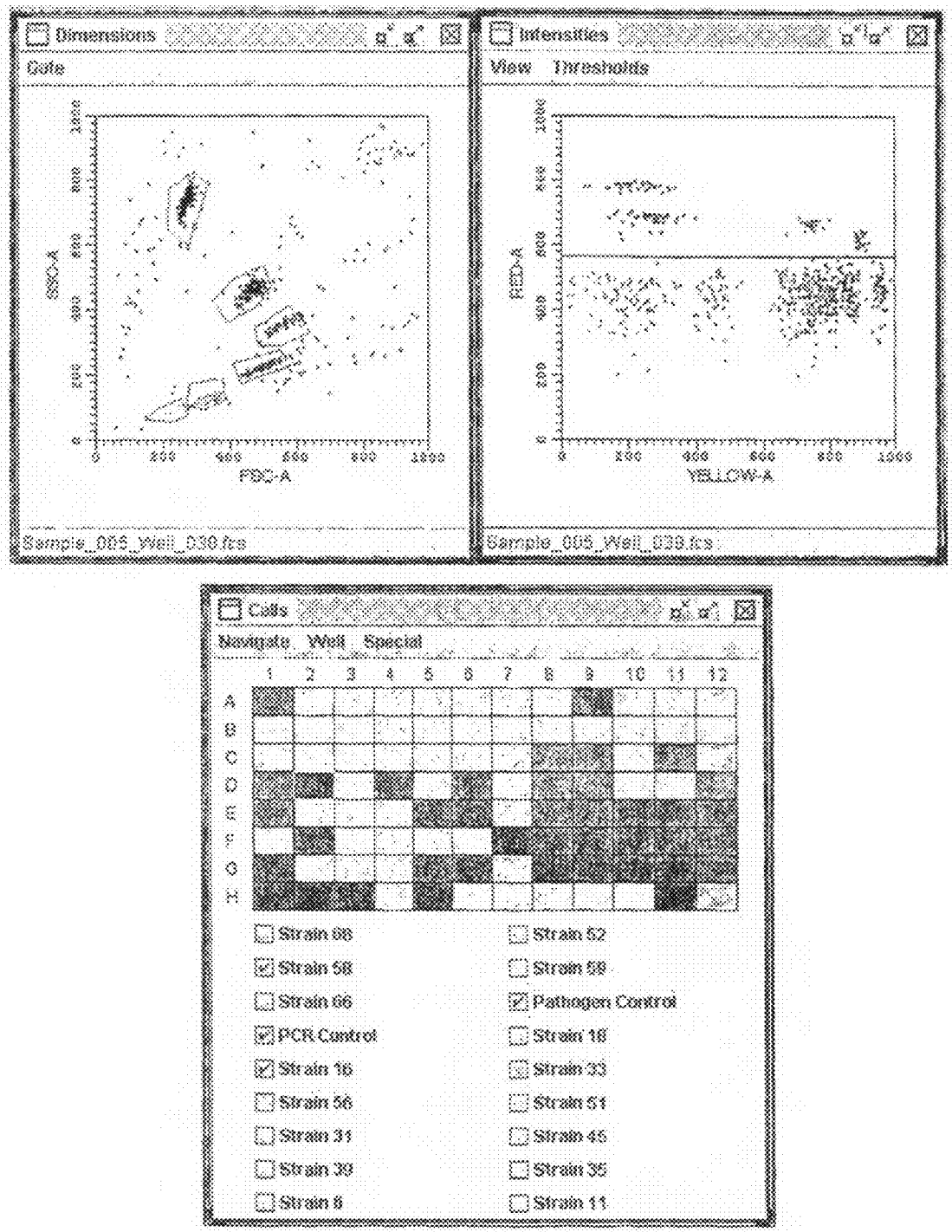
FIGURE 10C - Types 58 & 16

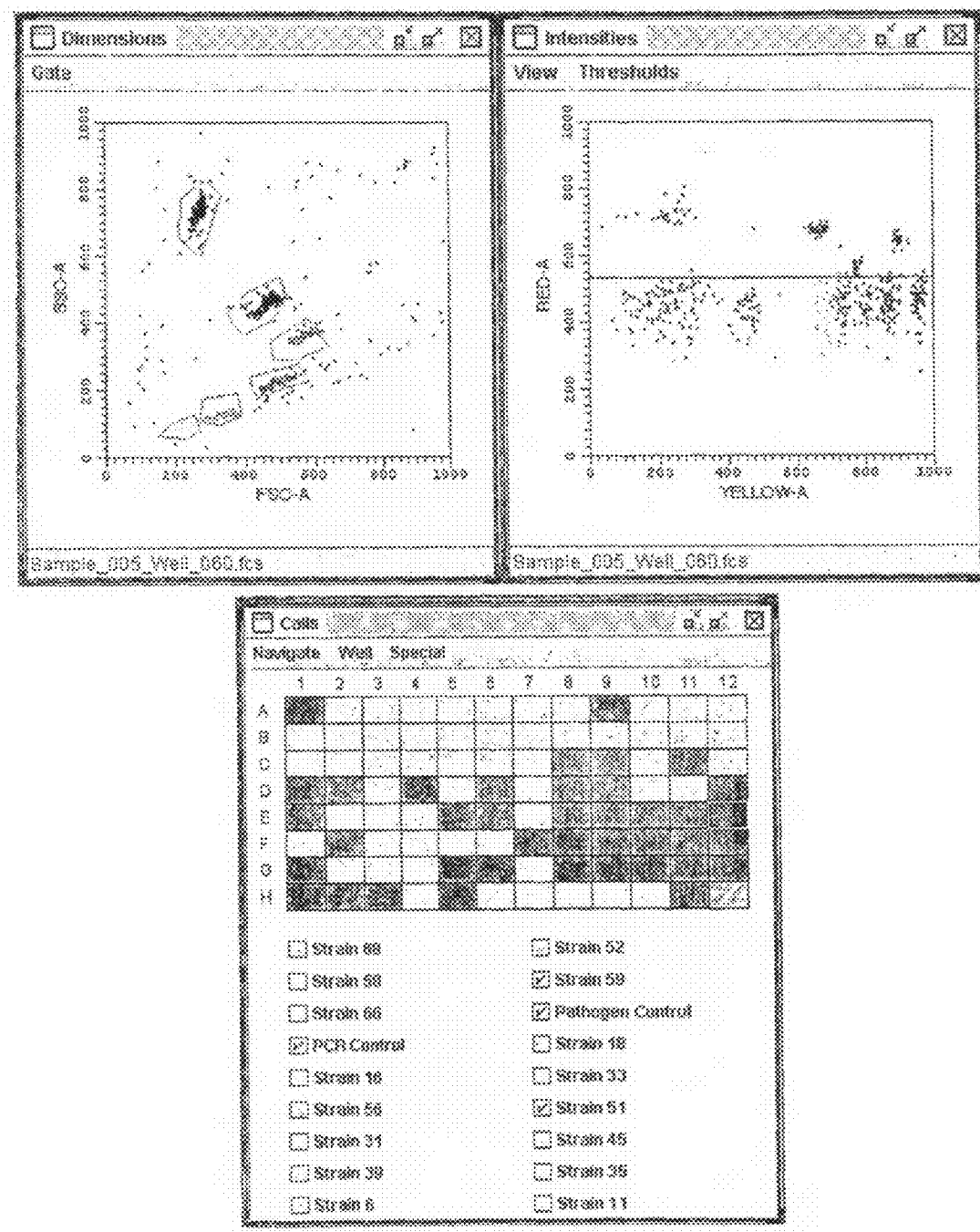
FIGURE 10D - Types 51 & 59

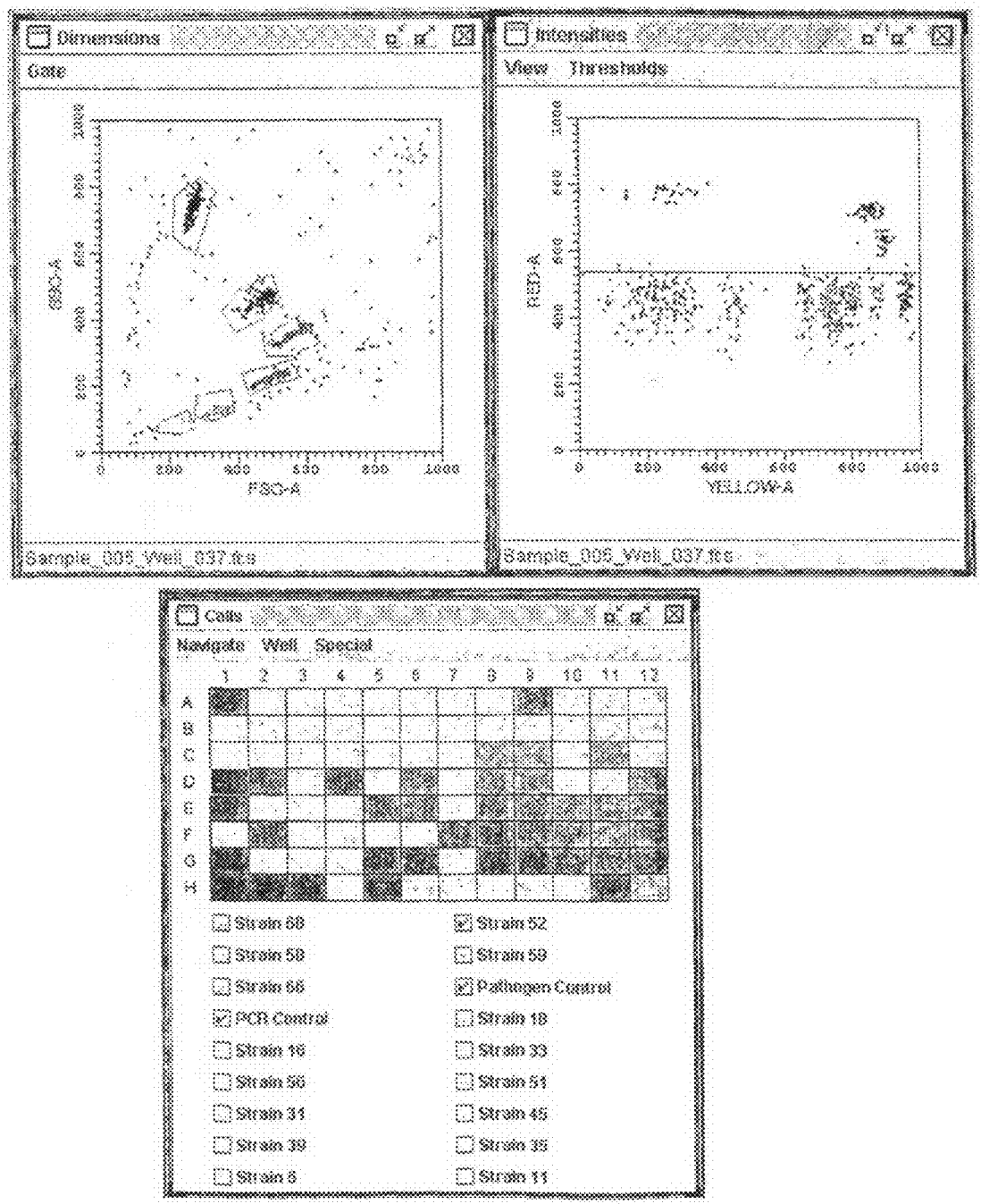
FIGURE 10E - Type 52

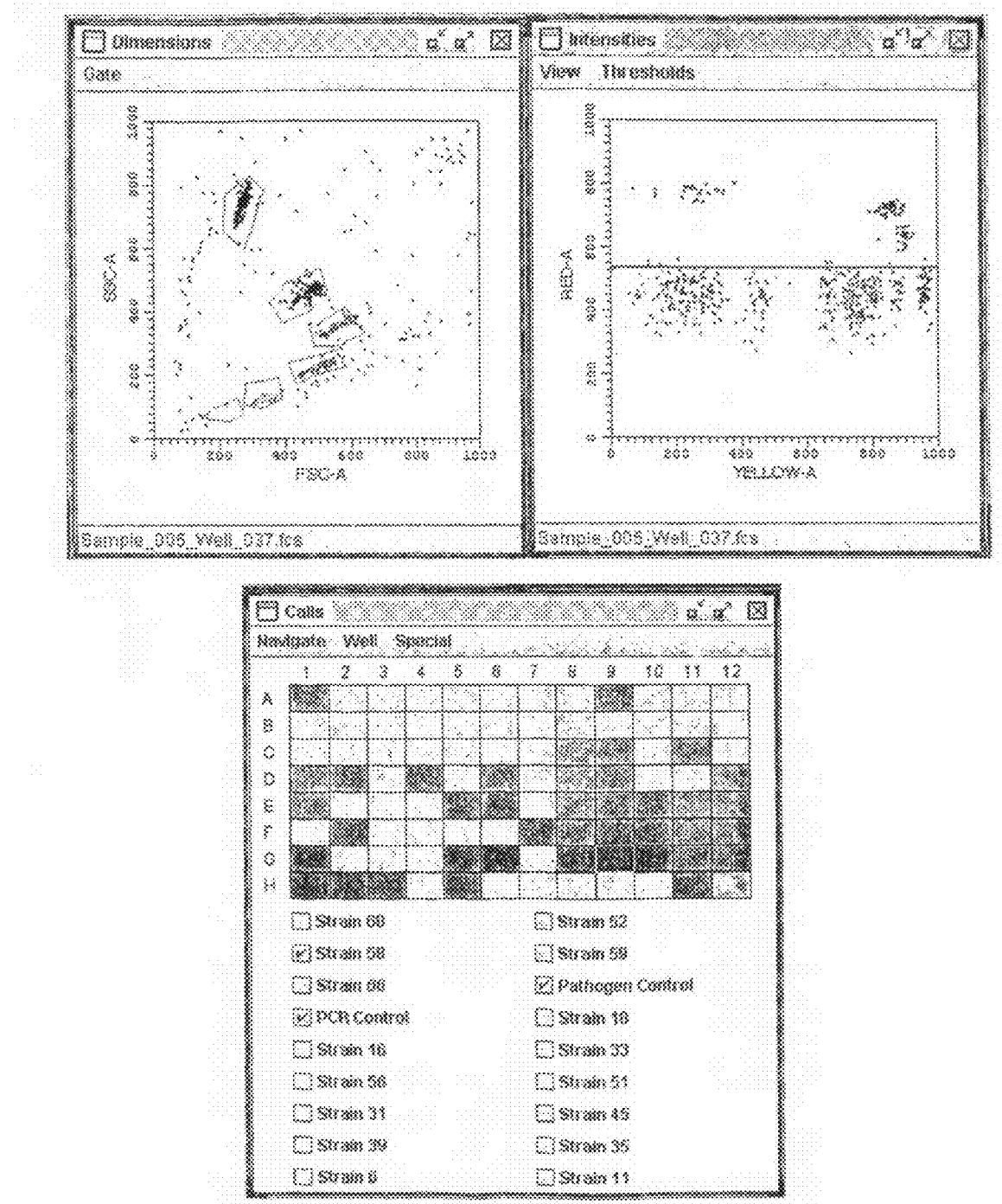
FIGURE 10F - Type 58

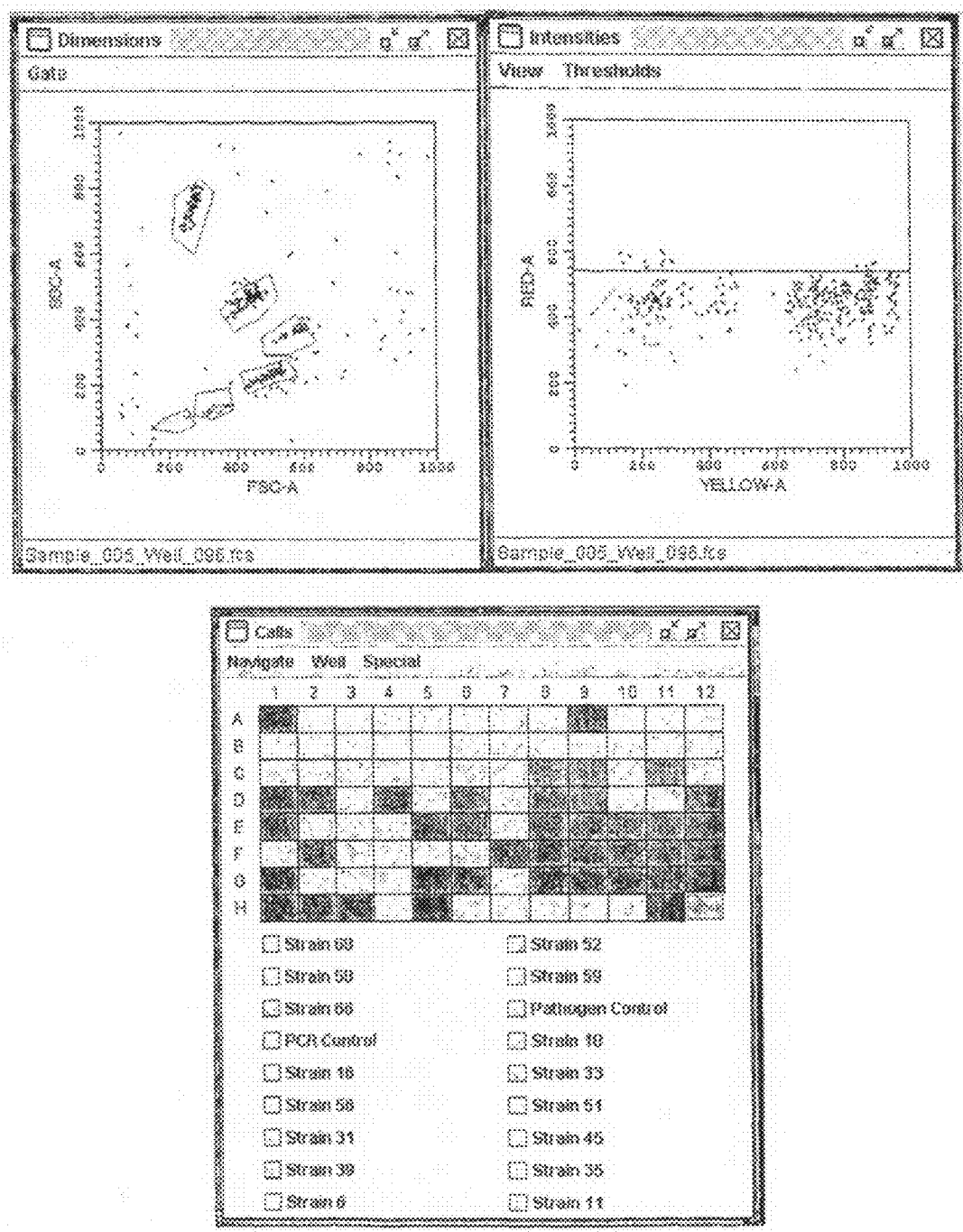
FIGURE 10G - Negative control (no DNA)

SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: oligonucleotide

<400> SEQUENCE: 1
tttgttactg tggtagatac tac                                           23

<210> SEQ ID NO 2
<211> LENGTH: 25
<212> TYPE: DNA
<213> ORGANISM: Artificial Sequence
<220> FEATURE:
<223> OTHER INFORMATION: oligonucleotide

<400> SEQUENCE: 2
gaaaaataaa ctgtaaatca tattc                                         25

<210> SEQ ID NO 3
<211> LENGTH: 20
<212> TYPE: DNA
<213> ORGANISM: Artificial Sequence
<220> FEATURE:
<223> OTHER INFORMATION: oligonucleotide

<400> SEQUENCE: 3
tacacacagg tgtacacaga                                               20

<210> SEQ ID NO 4
<211> LENGTH: 20
<212> TYPE: DNA
<213> ORGANISM: Artificial Sequence
<220> FEATURE:
<223> OTHER INFORMATION: oligonucleotide

<400> SEQUENCE: 4
accaagtact ctacgtgttg                                               20

<210> SEQ ID NO 5
<211> LENGTH: 65
<212> TYPE: DNA
<213> ORGANISM: Artificial Sequence
<220> FEATURE:
<223> OTHER INFORMATION: oligonucleotide

<400> SEQUENCE: 5
aattaaccct cactaaaggg aggacagcta tggacatccg taactacatc ttccacatac   60
accaa                                                               65

<210> SEQ ID NO 6
<211> LENGTH: 70
<212> TYPE: DNA
<213> ORGANISM: Artificial Sequence
<220> FEATURE:
<223> OTHER INFORMATION: oligonucleotide

<400> SEQUENCE: 6
aatggaatta accctcacta aagggaggac agctatggac atctgtgtct aaatctgcta   60
catacactaa                                                          70

```
<210> SEQ ID NO 7
<211> LENGTH: 70
<212> TYPE: DNA
<213> ORGANISM: Artificial Sequence
<220> FEATURE:
<223> OTHER INFORMATION: oligonucleotide

<400> SEQUENCE: 7
aatggaatta accctcacta aagggaggac agctatggac tgtttgtgct gcaattgcaa      60
acagtgatac                                                            70

<210> SEQ ID NO 8
<211> LENGTH: 70
<212> TYPE: DNA
<213> ORGANISM: Artificial Sequence
<220> FEATURE:
<223> OTHER INFORMATION: oligonucleotide

<400> SEQUENCE: 8
aatggaatta accctcacta aagggaggac agctatggac tttatgcaca caagtaacta      60
gtgacagtac                                                            70

<210> SEQ ID NO 9
<211> LENGTH: 70
<212> TYPE: DNA
<213> ORGANISM: Artificial Sequence
<220> FEATURE:
<223> OTHER INFORMATION: oligonucleotide

<400> SEQUENCE: 9
aatggaatta accctcacta aagggaggac agctatggac gtctgtgtgt tctgctgtgt      60
cttctagtga                                                            70

<210> SEQ ID NO 10
<211> LENGTH: 65
<212> TYPE: DNA
<213> ORGANISM: Artificial Sequence
<220> FEATURE:
<223> OTHER INFORMATION: oligonucleotide

<400> SEQUENCE: 10
aattaaccct cactaaaggg aggacagcta tggactctac ctctatagag tcttccatac      60
cttct                                                                 65

<210> SEQ ID NO 11
<211> LENGTH: 65
<212> TYPE: DNA
<213> ORGANISM: Artificial Sequence
<220> FEATURE:
<223> OTHER INFORMATION: oligonucleotide

<400> SEQUENCE: 11
aattaaccct cactaaaggg aggacagcta tggacacaca aaatcctgtg ccaagtacat      60
atgac                                                                 65

<210> SEQ ID NO 12
<211> LENGTH: 65
<212> TYPE: DNA
<213> ORGANISM: Artificial Sequence
<220> FEATURE:
<223> OTHER INFORMATION: oligonucleotide

<400> SEQUENCE: 12
```

```
aattaacccct cactaaaggg aggacagcta tggacagcac tgccactgct gcggtttccc    60
caaca                                                                 65
```

<210> SEQ ID NO 13
<211> LENGTH: 65
<212> TYPE: DNA
<213> ORGANISM: Artificial Sequence
<220> FEATURE:
<223> OTHER INFORMATION: oligonucleotide

<400> SEQUENCE: 13

```
aattaacccct cactaaaggg aggacagcta tggactgctg aggttaaaaa ggaaagcaca    60
tataa                                                                 65
```

<210> SEQ ID NO 14
<211> LENGTH: 65
<212> TYPE: DNA
<213> ORGANISM: Artificial Sequence
<220> FEATURE:
<223> OTHER INFORMATION: oligonucleotide

<400> SEQUENCE: 14

```
aattaacccct cactaaaggg aggacagcta tggacgtact gctacagaac agttaagtaa    60
atatg                                                                 65
```

<210> SEQ ID NO 15
<211> LENGTH: 70
<212> TYPE: DNA
<213> ORGANISM: Artificial Sequence
<220> FEATURE:
<223> OTHER INFORMATION: oligonucleotide

<400> SEQUENCE: 15

```
aatggaatta accctcacta aagggaggac agctatggac attatgcact gaagtaacta    60
aggaaggtac                                                            70
```

<210> SEQ ID NO 16
<211> LENGTH: 65
<212> TYPE: DNA
<213> ORGANISM: Artificial Sequence
<220> FEATURE:
<223> OTHER INFORMATION: oligonucleotide

<400> SEQUENCE: 16

```
aattaacccct cactaaaggg aggacagcta tggactctac tacttcttct attcctaatg    60
tatac                                                                 65
```

<210> SEQ ID NO 17
<211> LENGTH: 65
<212> TYPE: DNA
<213> ORGANISM: Artificial Sequence
<220> FEATURE:
<223> OTHER INFORMATION: oligonucleotide

<400> SEQUENCE: 17

```
aattaacccct cactaaaggg aggacagcta tggactctac tactactgaa tcagctgtac    60
caaat                                                                 65
```

<210> SEQ ID NO 18
<211> LENGTH: 65
<212> TYPE: DNA
<213> ORGANISM: Artificial Sequence
<220> FEATURE:

-continued

<223> OTHER INFORMATION: oligonucleotide

<400> SEQUENCE: 18 aattaacccct cactaaaggg aggacagcta tggacgtcat tatgtgctgc catatctact    60
tcaga    65

<210> SEQ ID NO 19
<211> LENGTH: 65
<212> TYPE: DNA
<213> ORGANISM: Artificial Sequence
<220> FEATURE:
<223> OTHER INFORMATION: oligonucleotide

<400> SEQUENCE: 19 aattaacccct cactaaaggg aggacagcta tggactgctt ctacacagtc tcctgtacct    60
gggca    65

<210> SEQ ID NO 20
<211> LENGTH: 51
<212> TYPE: DNA
<213> ORGANISM: Artificial Sequence
<220> FEATURE:
<223> OTHER INFORMATION: oligonucleotide

<400> SEQUENCE: 20
aaagggagga cagctatgga ctattaatgc agctaaaagc acattaacta a    51

<210> SEQ ID NO 21
<211> LENGTH: 51
<212> TYPE: DNA
<213> ORGANISM: Artificial Sequence
<220> FEATURE:
<223> OTHER INFORMATION: oligonucleotide

<400> SEQUENCE: 21
aaagggagga cagctatgga ccaaacacag acacagagag acccacagac a    51

<210> SEQ ID NO 22
<211> LENGTH: 58
<212> TYPE: DNA
<213> ORGANISM: Artificial Sequence
<220> FEATURE:
<223> OTHER INFORMATION: oligonucleotide

<400> SEQUENCE: 22 aattaacccct cactaaaggg aggacagcta tggactttgt tactgtggta gatactac    58

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
tacacacagg tgtacacaga    20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24

```
accaagtact ctacgtgttg                                                    20

<210> SEQ ID NO 25
<211> LENGTH: 23
<212> TYPE: DNA
<213> ORGANISM: Artificial Sequence
<220> FEATURE:
<223> OTHER INFORMATION: oligonucleotide
<220> FEATURE:
<221> NAME/KEY: variation
<222> LOCATION: (4)..(4)
<223> OTHER INFORMATION: k = g or t
<220> FEATURE:
<221> NAME/KEY: variation
<222> LOCATION: (9)..(9)
<223> OTHER INFORMATION: h = a, c or t
<220> FEATURE:
<221> NAME/KEY: variation
<222> LOCATION: (12)..(12)
<223> OTHER INFORMATION: k = g or t
<220> FEATURE:
<221> NAME/KEY: variation
<222> LOCATION: (15)..(15)
<223> OTHER INFORMATION: d = a, g or t
<220> FEATURE:
<221> NAME/KEY: variation
<222> LOCATION: (21)..(21)
<223> OTHER INFORMATION: y = t or c

<400> SEQUENCE: 25
tttkttachg tkgtdgatac yac                                                23

<210> SEQ ID NO 26
<211> LENGTH: 25
<212> TYPE: DNA
<213> ORGANISM: Artificial Sequence
<220> FEATURE:
<223> OTHER INFORMATION: oligonucleotide
<220> FEATURE:
<221> NAME/KEY: variation
<222> LOCATION: (5)..(5)
<223> OTHER INFORMATION: h = a, c or t
<220> FEATURE:
<221> NAME/KEY: variation
<222> LOCATION: (11)..(11)
<223> OTHER INFORMATION: y = t or c
<220> FEATURE:
<221> NAME/KEY: variation
<222> LOCATION: (14)..(14)
<223> OTHER INFORMATION: y = t or c
<220> FEATURE:
<221> NAME/KEY: variation
<222> LOCATION: (17)..(17)
<223> OTHER INFORMATION: d = a, g or t
<220> FEATURE:
<221> NAME/KEY: variation
<222> LOCATION: (23)..(23)
<223> OTHER INFORMATION: y = t or c

<400> SEQUENCE: 26
gaaahataaa ytgyaadtca taytc                                              25
```

HUMAN PAPILLOMA VIRUS (HPV) DETECTION USING NUCLEIC ACID PROBES, MICROBEADS AND FLUORESCENT-ACTIVATED CELL SORTER (FACS)

This application is U.S. National Phase of International Application PCT/AU2005/001865, filed Dec. 9, 2005 designating the U.S., and published in English as WO 2006/060872 on Jun. 15, 2006, which claims priority to Australian Patent Application No. 2004907070 filed Dec. 10, 2004 and U.S. provisional application 60/704,974 filed Aug. 3, 2005.

BACKGROUND OF THE INVENTION

1. Field of the Invention

The present invention relates generally to the field of diagnostic and detection assays. More particularly, the present invention provides methods, and reagents including biochips for detecting the presence of, or distinguishing between, one or more analytes in a sample.

2. Description of the Prior Art

Bibliographical details of references provided in the subject specification are listed at the end of the specification.

Reference to any prior art in this specification is not, and should not be taken as, an acknowledgement or any form of suggestion that this prior art forms part of the common general knowledge in any country.

The need for rapid and reliable screening methods for detecting multiple analytes in a single assay is vital not only in the fields of clinical diagnosis, but also for use in screening, for example, for environmental toxins and drug screening.

One such area which is desperately in need of improved screening methods and reagents is in the field of infectious diseases. For example, a conservative estimate of the world use of diagnostic tests for sexually transmitted diseases, such as Human Papilloma Virus (HPV), is approximately 20,000,000 tests per year.

Many of the existing tests for screening for the causes of infectious diseases are time consuming, labor intensive, expensive, often specific for only one specific pathogen and/or cannot differentiate between different strains of pathogens.

HPV is the main causative pathogen for cervical cancer. However, the HPV taxon comprises many "strains" of the pathogen, only some of which are associated with the development of cervical cancer and other carcinomas. Accordingly, the strains of HPV are typically classified as either "high risk" strains, including the 13 strains which account for roughly 98% of cervical cases, or "low risk" strains which are not typically associated with the development of cervical cancer.

Currently, cervical cancer is detected by a Pap smear. In this technique, cells are collected from the cervix by scraping or washing. These cells are then placed on a glass microscope slide to produce the "smear". A pathologist then examines the slide, looking for aberrant cells. The Pap smear, however, is a somewhat unsatisfactory assay for unequivocally determining cervical cancer risk, as the technique has a false negative rate of approximately 20% and the technique cannot distinguish "high risk" and "low risk" taxon.

In accordance with the present invention, a detection assay is provided which is able to detect an analyte in a sample and/or differentiate a number of different analytes. Furthermore, the reagents and methods of present invention described herein are relatively rapid and inexpensive compared to some existing detection assays.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides assays which enable the detection of one or more analytes and/or which differentiate between members within a class of analytes. In particular, multiplexing analysis based on the properties of the analytes and of the assay components is employed to identify or distinguish between analytes.

Accordingly, one aspect of the present invention provides a beadset for detecting one or more analytes and/or for differentiating between two or more members within a class of analytes, wherein the beadset comprises a plurality of subsets of beads wherein:
  (a) the beads of each subset are homogeneous with respect to size;
  (b) the beads within each subset are coupled to a reactant that will specifically react with a given analyte of interest in a sample to be tested;
  (c) the reactant on each bead is labeled with the same label with each subset of beads having a different fluorescent intensity to create a heterogeneous mixture of subsets of beads based on fluorescent intensity; and
  (d) at least two subsets of beads are mixed together to produce a beadset, wherein the subset identity and therefore the reactant to which the bead has been coupled is identifiable by flow cytometry based on size, fluorescent intensity and analyte discrimination.

In another aspect, the present invention contemplates a method for detecting and/or differentiating between two or more analytes in a sample, comprising the steps of:
  (a) contacting the sample with a beadset specific for the analytes of interest;
  (b) incubating said beadset with said sample for a time and under conditions sufficient to allow said analyte(s) in said sample to react specifically with a reactant on a bead within said beadset; and
  (c) detecting and/or differentiating analytes in the sample which are bound to a reactant on said bead.

In a related aspect, the reactants can be labeled with one or more flurochromes that further allow differentiation between members within a class of analytes. In a preferred aspect, the present invention provides methods and beadsets which are able to detect and/or distinguish between analytes within a biological sample, wherein the analytes are specific for an infectious pathogen.

Biological samples contemplated herein include blood, serum, saliva, faeces, urine, tissue fluid, semen, exudate, pus, respiratory fluid and mucus and swabs from topical sores, cancers and lesions.

The term "pathogen" refers to a microorganism or virus which infects or colonizes a sample. Exemplary pathogens include viruses, bacteria, fungi and eukaryotic microorganisms. A virus includes a Lentivirus (e.g. AIDS virus, HIV-I, HIV-II, HTLV-IV), Retrovirus and avian flu virus. In a preferred embodiment, "pathogen" includes a microorganism or virus which infects a multicellular organism such as an animal or plant. Accordingly, in one embodiment, the analyte may be regarded as an animal or plant pathogen. However, the present invention encompasses the detection and/or differentiation of non-pathogenic entities which colonize multicellular organisms such as symbionts, endophytes, gastrointestinal colonists and the like. The methods of the present invention are also applicable to the detection of analytes in a sample which are indicative of the presence of therapeutic agents or substances of abuse. The methods and reagents of the present invention can also be used in the detection of an analyte is a sample which is not derived from a biological sample isolated from an animal or a plant. As such, the reagents and methods of the present invention also extend to the detection of one or more analytes and/or differentiation between analytes in environmental samples, including air, water and soil samples, including extraterrestrial soil, dust or like samples industrial samples and the like in addition to the biological samples listed above.

In one particular embodiment, the present invention provides for diagnostic methods and reagents for HPV in human subjects and is able to detect and differentiate between different strains in order to distinguish "high risk" HPV taxon from "low risk" HPV taxon. Accordingly, in one particularly preferred embodiment, the present invention provides beadsets which are able to distinguish between pluralities of different HPV strains. As such, in one aspect, the analytes are specific for a plurality of HPV taxons and the methods and reagents are specific for the detection of nucleic acid or antigens or antibodies which are specific for the plurality of HPV taxons.

In an even more particular embodiment, nucleic acid primers or probes capable of binding to a strain-specific portion of an HPV genome are immobilized onto beads in each bead subset. Primers directed to conserved regions within an HPV genome flanking a strain-specific region are then used to amplify the HPM genome. Subsets of beads specific for any one strain of HPV are then used to detect or distinguish the HPV strain.

Hence, another aspect of the present invention is directed to a beadset for detecting one or more strains of HPV and/or for differentiating between two or more strains of HPV, wherein the beadset comprises a plurality of subsets of beads wherein:
(a) the beads of each subset are homogenous with respect to size;
(b) the beads within each subset are coupled to a nucleic acid capture probe which is capable of binding to a HPV strain-specific region of an HPV genome;
(c) the capture probe on each bead is labeled with the same label with each subset of beads having a different fluorescent intensity to create a heterogeneous mixture of beads based on fluorescent intensity; and
(d) at least two subsets of beads are mixed together to produce a beadset, wherein the subset identity and therefore the strain of HPV is identifiable by flow cytometry based on size, fluorescent intensity and sequence discrimination.

Another aspect of the present invention contemplates a method for detecting and/or differentiating between two or more HPV strains in a sample, comprising the steps of:
(a) contacting the sample with a beadset comprising a plurality of subsets of beads wherein:
(i) the beads of each subset are homogenous with respect to size; t
(ii) the beads within each subset are coupled to a nucleic acid capture probe which is capable of binding to a HPV strain-specific region of an HPV genome;
(iii) the capture probe on each bead is labeled with the same label with each subset of beads having a different fluorescent intensity to create a heterogeneous mixture of beads based on fluorescent intensity; and
(iv) at least two subsets of beads are mixed together to produce a beadset, wherein the subset identity and therefore the strain of HPV is identifiable by flow cytometry based on size, intensity and sequence discrimination;
(b) incubating said beadset with said sample for a time and under conditions sufficient to allow said probes to bind to the HPV genome amplified to generate a replicon comprising a strain-specific region;
(c) detecting and/or differentiating the amplicons generated in the sample which are bound to said beads to thereby identify or distinguish between the two or more HPV strains.

In a preferred aspect, the beads within the beadsets are distinguishable on the basis of size, the level of fluorescent intensity, the type of flurochrome and the reactant which is capable of reacting with a specific analyte.

The method of the present invention in relation to HPV detection may be used to distinguish to between from 2 and 16 trains of HPV including between 2, 3, 4, 5, 6, 7, 8, 9, 10, 11, 12, 13, 14, 15 and 16 strains. In a particularly preferred embodiment, the beadset comprises at least 16 subsets of beads for HPV strains 6, 11, 16, 18, 31, 33, 35, 39, 45, 51, 52, 56, 58, 59, 66 and 68. Suitable capture probes are those listed in FIG. 9 and represented in SEQ ID NOs:5 through 20.

Determination of whether binding has occurred between an analyte and a reactant present on a bead may be done using any methodology which allows the differentiation between different beads within the beadset. In a particularly preferred embodiment, the method of differentiating between different beads within the beadsets is flow cytometry.

The present invention further contemplates diagnostic kits for use in accordance with the reagents and methods of the present invention. In particular, the present invention extends to biochips and the miniaturization of the solid phase components of the assay to generate nanoassay reagents. In one embodiment, the bead set or part thereof or other reagents are immobilized to a solid phase such as a biochip. The biochip may also be regarded as a "biolab" on which at least part of the assay is performed and/or results recorded. A list of abbreviations used herein is provided in Table 1.

TABLE 1

| Abbreviation | Description |
|---|---|
| | Abbreviations |
| FITC | Fluorescein |
| HEX | Hexachlorofluorescein |
| HIV | Human Immunodeficiency Virus |
| HPV | Human Papilloma Virus |
| JOE | 7'-dimethoxyfluorescein |
| PCR | Polymerase chain reaction |
| PE | Phycoerythrin |
| PMT | Photomultiplier tube |
| QD | Quantum dot |
| TAMRA | Carboxytetrametylrhodamine |
| TET | Teterachlorofluoresceine |
| TMR | Tetramethylrhodamine |
| VRE | Vancomycin resistant enterococci |

A summary of the sequence identifiers used herein are shown in Table 2.

TABLE 2

Sequence Identifiers

| Sequence Identifier | Sequence |
| --- | --- |
| SEQ ID NO: 1 | GP5+ primer nucleotide sequence |
| SEQ ID NO: 2 | GP6+ primer nucleotide sequence |
| SEQ ID NO: 3 | LC1_F primer nucleotide sequence |
| SEQ ID NO: 4 | LC1_R primer nucleotide sequence |
| SEQ ID NO: 5 | Capture probe or HPV strain 6 |
| SEQ ID NO: 6 | Capture probe or HPV strain 11 |
| SEQ ID NO: 7 | Capture probe or HPV 31 |
| SEQ ID NO: 8 | Capture probe or HPV 33 |
| SEQ ID NO: 9 | Capture probe or HPV 35 |
| SEQ ID NO: 10 | Capture probe or HPV 39 |
| SEQ ID NO: 11 | Capture probe or HPV 45 |
| SEQ ID NO: 12 | Capture probe or HPV 51 |
| SEQ ID NO: 13 | Capture probe or HPV 52 |
| SEQ ID NO: 14 | Capture probe or HPV 56 |
| SEQ ID NO: 15 | Capture probe or HPV 58 |
| SEQ ID NO: 16 | Capture probe or HPV 59 |
| SEQ ID NO: 17 | Probe 68 primer HPV synthetic |
| SEQ ID NO: 18 | Capture probe or HPV 16 |
| SEQ ID NO: 19 | Capture probe or HPV 18 |
| SEQ ID NO: 20 | Capture probe or HPV 66 |
| SEQ ID NO: 21 | MLC1_Ac primer HPV synthetic |
| SEQ ID NO: 22 | GP5+ For_Ac primer HPV synthetic |
| SEQ ID NO: 23 | MLC1_reg_FP primer HPV synthetic |
| SEQ ID NO: 24 | MLC1_reg_R primer HPV synthetic |
| SEQ ID NO: 25 | GP5d+ primer HPV synthetic |
| SEQ ID NO: 26 | GP6d+ primer HPV synthetic |

BRIEF DESCRIPTION OF THE FIGURES

FIG. 7 is a graphical representation showing how 17 binding agents were distinguished using flow cytometry on the basis of particle size and fluorescent label intensity. Clusters 1 to 4 correspond to 6.8 µm particles with label intensities of 0%, 4%, 20% and 100% respectively; Clusters 5 to 8 correspond to 5.6 µm particles with label intensities of 0%, 4%, 20% and 100% respectively; Clusters 9 to 11 correspond to 5.0 µm particles with label intensities of 100%, 20% and 0% respectively; Clusters 12 and 13 correspond to 4.1 µm particles with label intensities of 100% and 0% respectively; Clusters 14 and 15 correspond to 3.5 µm particles with label intensities of 100% and 0% respectively; Clusters 16 and 17 correspond to 3.0 µm particles with label intensities of 0% and 100% respectively.

FIG. 9 is a representation of capture probes (primers) specific for HPV strains 6, 11, 16, 18, 31, 33, 35, 39, 45, 51, 52, 56, 58, 59, 66 and 68.

FIGS. 10A through G provide Qplots (trade mark) of human samples detecting the presence or absence of HPV.

DETAILED DESCRIPTION OF THE INVENTION

Figure 1:
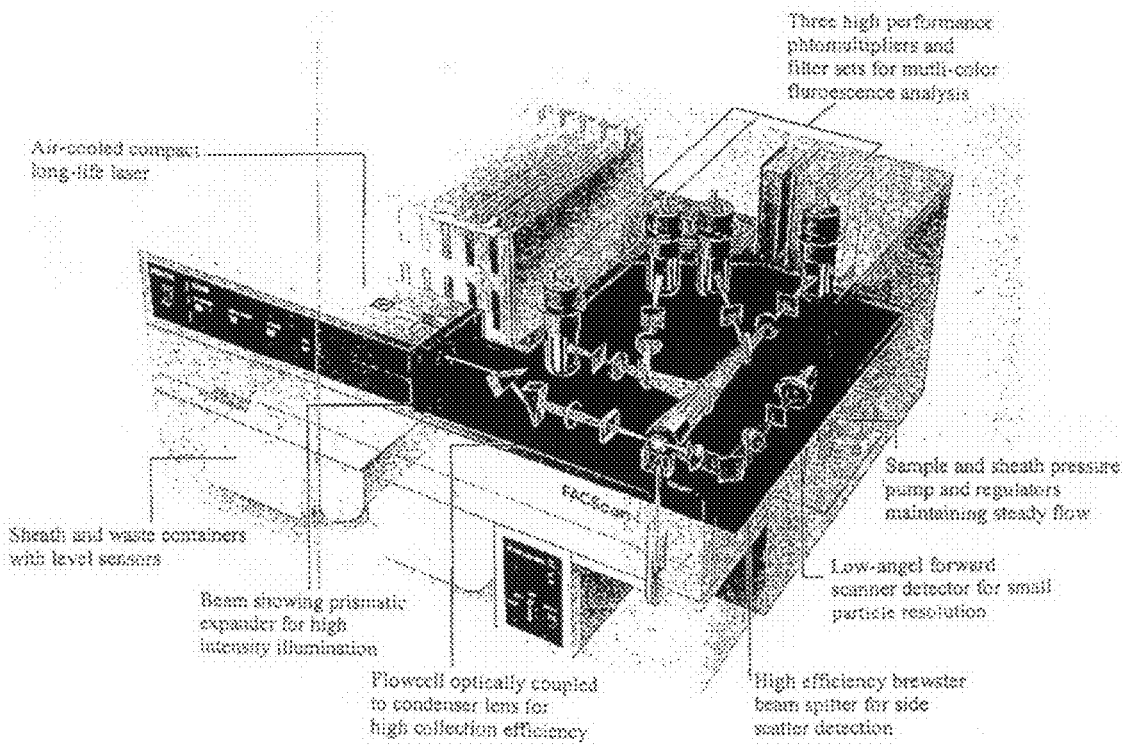
FIG. 1 is a graphical representation depicting a typical flow cytometer.

The present invention provides assays and reagents including biochips which enable the detection of one or more analytes and/or to differentiate between members within a class of analytes. In particular, analytes are identified or distinguished by a method of multiplexing analysis based on the properties of the analytes and of the assay components. The diagnostic and detection assays and reagents of the present invention have particular application in the diagnosis of pathogen infections in multicellular eukaryotic subjects. In one particular embodiment, the present invention provides a diagnostic assay for HPV in human subjects and is able to differentiate between HPV taxons in order to distinguish "high risk" HPV infections from "low risk" HPV infections. Furthermore, the present invention also provides a method of diagnosing or assessing the risk of development of a disease associated with an infection by an analyte in a multicellular eukaryotic subject including, inter alia, cervical cancer in a human subject.

It is to be understood that unless otherwise indicated, the subject invention is not limited to specific diagnostic or assay protocols, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context already dictates otherwise. Thus, for example, reference to "an analyte" includes a single analyte as well as two or more analytes; a "physiochemically distinguishable substrate" includes a single substrate as well as two or more substrates; and so forth.

Accordingly, in one aspect, the present invention provides a beadset which is capable of detecting, and/or differentiating between two or more analytes in a sample, said beadset comprising:

(a) the beads of each subset are homogeneous with respect to size;

(b) the beads within each subset are coupled to a reactant that will specifically react with a given analyte of interest in a sample to be tested;

(c) the reactant on each bead is labeled with the same label with each subset of beads having a different fluorescent intensity to create a heterogeneous mixture of subsets of beads based on fluorescent intensity; and (d) at least two subsets of beads are mixed together to produce a beadset, wherein the subset identity and therefore the reactant to which the bead has been coupled is identifiable by flow cytometry based on size, fluorescent intensity and analyte discrimination.

In a related aspect, the reactants may be further differentially labeled to create additional subpopulations of beads based on the incorporation of different flurochromes.

In another aspect, the present invention provides methods or beadsets for the detection and/or differentiation of an analyte.

In a preferred aspect, the methods or beadsets of the present invention are able to detect and/or differentiate pathogenic analytes.

The present invention also provides methods for detecting and/or differentiating between one or more analytes in a sample comprising the steps of:

(a) contacting the sample with a beadset specific for the analytes of interest;

(b) incubating said beadset with said sample for a time and under conditions sufficient to allow said analyte(s) in said sample to react specifically with a reactant on a bead within said beadset; and (c) detecting and/or differentiating analytes in the sample which are bound to a reactant on said bead.

As used herein, the term "pathogenic analyte" refers to a microorganism or virus which putatively infects, colonizes or has otherwise contaminated the sample. Exemplary pathogen analyte include viruses, bacteria, fungi and eukaryotic microorganisms. In a preferred embodiment, "analyte" includes a microorganism or virus which infects a multicellular organism such as an animal or plant. Accordingly, in one embodiment the pathogenic analyte may be regarded as an animal or plant pathogen. However, the present invention encompasses the detection and differentiation of non-pathogenic analyte which colonize multicellular organisms such as microbial symbionts of animals (eg. *Lactobacillus* spp., ruminant bacteria), microbial symbionts of insects (eg. *Streptomyces* spp., *Wolbachia* spp.), microbial symbionts of sponges (eg. green algae, dinoflagellates, cyanobacteria) and the like; endophytes of plants (eg. Mycorrhiza, *Rhizobium* spp., *Frankia* spp., *Streptomyces* spp.); and the like. Furthermore, the analyte may be an analyte which is not associated with a multicellular organism. Such analytes include bacteria, fungi, viruses, protists, nematodes and the like which colonize particular environments including "natural" environments such as soil, oceans, fresh water, ice, rock, hydrothermal vents and air; health care environments including hospitals, hospital equipment, surgical equipment, health care staff garments and the like; "industrial" environments including manufacturing facilities, pharmaceutical facilities, breweries, wineries and the like; "laboratory" environments including fermenters, cultures, benches, equipment and the like.

Accordingly, samples contemplated by the present invention include industrial samples such as air, water and soil and the like and biological samples such as blood, serum, saliva, faeces, urine, tissue fluid, semen, exudate, pus, respiratory fluid and mucus and swabs from topical sores, cancers and lesions. In addition, a sample may be an extraterrestrial sample such as from a meteorite or on another planet. In regards to the latter, the assay of the present invention may be adapted for use on an interplanetary remote vehicle for testing of soil or dust or ice samples or for testing core material in a planet.

In one preferred embodiment, the analyte comprises a bacterium, fungus, virus and/or eukaryotic parasite which infects an animal subject. "Animal subjects" contemplated herein include any animal, preferably a mammal and more preferably a primate including a lower primate and even more preferably, a human. For convenience, an "animal" also specifically includes livestock species such as cattle, horses, sheep, pigs, goats and donkeys as well as laboratory animals including mice, rats, rabbits, guinea pigs and hamsters.

Exemplary human analytes which may be detected using the reagents and methods of the present invention include viruses such Human papilloma virus (HPV), coronaviruses including the SARS virus, influenza viruses, avian flue virus, HIV including HIV-1, HIV-II or HLTV-IV, Lentiviruses in general, hepatitis viruses and the like, the pathogenic agents of sexually transmitted diseases such as Chlamydia, Gonorrhoea, *Mycoplasma* spp. and Syphilis; Food-borne pathogens such as *Listeria* spp., *Salmonella* spp., *E. coil* (particularly *E. coli* HO 567), *Shigella* spp., *Brucella* spp., *Staphylococcus aureus*; Nosicomial pathogens such as *S. aureus* including Methicillin-Resistant *S. Aureus* (MRSA) and enterococci including Vancomycin Resistant Enterococci (VRE); Environmentally acquired pathogens such as *Legionella* spp., *Giardia* spp., *Crytospiridium* spp., *Bacillus anthacis* (anthrax) and the like.

In one aspect, the sample in which the analyte is detected is preferably a sample derived from a multicellular subject which is putatively infected or colonized by the analyte. Therefore, in one aspect, the sample is preferably a "biological sample". Exemplary biological samples which in no way limit the present invention include tissue or cell samples such as cell scapes, biopsies and the like and body fluid samples including blood, urine, lymph, amniotic fluid, cerebrospinal fluid and the like.

In another aspect, the methods of the present invention are also applicable to the detection of a "analyte" in a sample which is not exclusively derived from a multicellular eukaryotic organism. As such, the present invention extends to detecting, and/or differentiating between, one or more particular taxons or strains of analytes in samples such as environmental samples (including air, water and soil samples), industrial samples, laboratory samples and the like. For example, the methods of the present invention may be used to assess the prokaryotic microflora, eukaryotic microflora and or viral load of a soil, water or air sample or a sample derived from a man-made object or surface.

In one particularly preferred embodiment of the present invention, the analyte to be detected is HPV or a strain thereof and the sample is preferably a biological sample derived from a human subject. In a further preferred embodiment, the biological sample comprises one or more cells of the subject, blood or urine. Most preferably, the biological sample comprises cervical cells collected from the subject.

HPV is described in detail by Gearhart et al. (www.emedicine.com/MED/topic1037.htm, 2004) which is reproduced in part below. HPVs produce epithelial tumors of the skin and mucous membranes. Over 100 HPV types have been detected, and the genomes of almost 70 have been sequenced completely. The current classification system, which is based on similarities in their genomic sequences, generally correlates with the 3 categories used to describe HPV clinically: anogenital and/or mucosal, nongenital cutaneous, and epidermodysplasia verruciformis (EV). A database of HPV genomic sequences and a phylogenic tree are available via the Internet at HPV Sequence Database.

The mucosal HPV infections are classified further as latent (asymptomatic), subclinical, or clinical. Clinical lesions are grossly apparent, whereas latent infections are detected only by tests for viral DNA. Subclinical lesions are identified by application of 5% acetic acid and inspection under magnification. Most HPV infections are latent; clinically apparent infections usually result in warts rather than malignancies.

HPV types 6 and 11 are typically labeled as low risk because infection with these types has low oncogenic potential and usually results in the formation of condylomata and low-grade precancerous lesions. HPV types 16 and 18 have emerged as the high-risk types of HPV because they are responsible for most high-grade intraepithelial lesions that may progress to carcinomas, particularly those in the anogenital and/or mucosal category.

HPV infection alone does not cause malignant transformation of infected tissue. Cofactors, such as tobacco use, ultraviolet radiation, pregnancy, folate deficiency, and immune suppression have been implicated in this process. Table 3 lists a variety of diseases and the associated HPV subtypes.

TABLE 3

Diseases and Associated HPV Subtypes

| | HPV Type |
|---|---|
| Nongenital Cutaneous Disease | |
| Common warts (verrucae vulgaris) | 1, 2, 4, 26, 27, 29, 41, 57, 65 |
| Plantar warts (myrmecias) | 1, 2, 4, 63 |
| Flat warts (verrucae plana) | 3, 10, 27, 28, 38, 41, 49 |
| Butcher's warts (common warts of people who handle meat, poultry, and fish) | 1, 2, 3, 4, 7, 10, 28 |
| Mosaic warts | 2, 27, 57 |
| Ungual squamous cell carcinoma | 16 |
| Epidermodysplasia verruciformis (benign) | 2, 3, 10, 12, 15, 19, 36, 46, 47, 50 |
| Epidermodysplasia verruciformis (malignant or benign) | 5, 8, 9, 10, 14, 17, 20, 21, 22, 23, 24, 25, 37, 38 |
| Nonwarty skin lesions | 37, 38 |
| Nongenital Mucosal Disease | |
| Respiratory papillomatosis | 6, 11 |
| Squamous cell carcinoma of the lung | 6, 11, 16, 18 |
| Laryngeal papilloma | 6, 11, 30 |
| Laryngeal carcinoma | 16, 18 |
| Maxillary sinus papilloma | 57 |
| Squamous cell carcinoma of the sinuses | 16, 18 |
| Conjunctival papillomas | 6, 11 |
| Conjunctival carcinoma | 16 |
| Oral focal epithelial hyperplasia (Heck disease) | 13, 32 |
| Oral carcinoma | 16, 18 |
| Oral leukoplakia | 16, 18 |
| Squamous cell carcinoma of the esophagus | 16, 18 |
| Anogenital Disease | |
| Condylomata acuminata | 6, 11, 30, 42, 43, 44, 45, 51, 52, 54 |
| Bowenoid papulosis | 16, 18, 34, 39, 42, 45 |
| Bowen disease | 16, 18, 31, 34 |
| Giant condylomata (Buschke-Löwenstein tumors) | 6, 11 |
| Unspecified intraepithelial neoplasia | 30, 34, 39, 40, 53, 57, 59, 61, 62, 64, 66, 67, 68, 69 |
| Low-grade intraepithelial neoplasia | 6, 11, 43 |
| Intermediate intraepithelial neoplasia | 31, 33, 35, 42, 44, 45, 51, 52 |
| High-grade intraepithelial neoplasia | 16, 18, 56, 58 |
| Carcinoma of vulva | 6, 11, 16, 18 |
| Carcinoma of vagina | 16 |
| Carcinoma of cervix | 16, 18, 31 |
| Carcinoma of anus | 16, 31, 32, 33 |
| Carcinoma in situ of penis (erythroplasia of Queyrat) | 16 |
| Carcinoma of penis | 16, 18 |

Papillomaviruses are highly species specific and do not infect other species, even under laboratory conditions. Humans are the only known reservoir for HPV.

Papillomaviruses are nonenveloped viruses of icosahedral symmetry with 72 capsomeres that surround a genome containing double-stranded circular DNA with approximately 8000 base pairs.

Papillomaviruses are thought to have 2 modes of replication, ie. stable replication of the episomal genome in basal cells and runaway, or vegetative, replication in more differentiated cells to generate progeny virus. Although all cells of a lesion contain the viral genome, the expression of viral genes is tightly linked to the state of cellular differentiation. Most viral genes are not activated until the infected keratinocyte leaves the basal layer. Production of virus particles can occur only in highly differentiated keratinocytes; therefore, virus production only occurs at the epithelial surface where the cells are ultimately sloughed into the environment.

HPV lesions are thought to arise from the proliferation of infected basal keratinocytes. Infection typically occurs when basal cells are exposed to infectious virus through a disturbed epithelial barrier as would occur during sexual intercourse or after minor skin abrasions. HPV infections have not been shown to be cytolytic, rather viral particles are released as a result of degeneration of desquamating cells. Furthermore, the HPV virus can survive for many months and at low temperatures without a host.

Virus multiplication is generally confined to the nucleus. Consequently, infected cells usually exhibit a high degree of nuclear atypia. Koilocytosis (from the Greek koilos, meaning empty) describes a combination of perinuclear clearing (halo) with a pyknotic or shrunken (rasinoid) nucleus and is a characteristic feature of productive papillomavirus infection.

The HPV genome exists as a circular episomal DNA separate from the host cell nucleus in benign or low-risk HPV lesions, such as those typically associated with HPV types 6 and 11. The genomes of high-risk HPV types 16 and 18 are typically integrated into the host cell DNA in malignant lesions. The present invention, however, extends to any strain of HPV including but not limited to strains 6, 11, 16, 18, 31, 33, 35, 39, 45, 51, 52, 56, 58, 59, 66 and 68. Integration of the viral genome into the host cell genome is considered a hallmark of malignant transformation. HPV proteins E6 and E7 of high-risk serotypes have been shown to inactivate the host's tumor suppressor proteins p53 and Rb, thereby resulting in unregulated host cell proliferation and malignant transformation.

Therefore, in another aspect, the present invention provides a method for detecting, and/or differentiating between, one or more particular strains of HPV in a biological sample, said method comprising the steps of:
  (i) obtaining a biological sample which putatively comprises HPV from a human subject;
  (ii) isolating nucleic acid from said sample;
  (iii) amplifying the nucleic acid from said sample using primers which generate an amplicon which is distinct for each strain of HPV;

(iv) optionally amplifying a control nucleic acid sequence;
(v) effecting labeling of the amplicon(s) recited at steps (iii) and/or (iv);
(vi) hybridizing the labeled amplicon(s) to a beadset coated with reactants wherein each member of the beadset comprises a nucleic acid molecule having complementarity to a nucleotide sequence of a particular strain of HPV, bound or otherwise associated with a physiochemically distinguishable bead; and
(vii) determining to which of the reactants an amplicon has bound;

wherein the association of an amplicon with a particular reactant is indicative of the presence of a particular strain of HPV in the sample.

The present invention enables the detection of amplified HPV DNA or, with the use of a reverse transcriptase, corresponding RNA. Hence, the present invention contemplates beads with RNA or DNA or chemical analogs thereof.

The method of the present invention is predicated, in part, on detecting and/or differentiating between one or more particular strains of a subject analyte in a sample. Reference herein to "particular strains of a subject analyte" includes any variants of the species or taxon of the analyte. Examples of "strains" of an analyte include sub-species of the analyte, variants of the analyte with differing levels of virulence, variants of the analyte which indicate different prognoses when infecting or colonizing a host, biochemical variants of the analyte and the like.

In one preferred embodiment, the method of the present invention may be adapted to detecting and/or differentiating between particular strains of HPV which are associated with higher risk or higher oncogenic potential in humans (high risk strains) and those which are associated with lower carcinoma risk or low oncogenic potential (low risk strains). Accordingly, the term "high risk" strain of HPV includes any strain of HPV which is associated with the development of carcinoma, including cervical cancer, in human subjects. As indicated above, exemplary high risk strains of HPV which in no way limits the invention include HPV 6, 11, 16, 18, 31, 33, 35, 39, 45, 51, 52, 56, 58, 59, 66 and 68. Suitable capture probes on the beads for these strains of HPV are shown in FIG. 9. The term "probe" and "primer" may be used interchangeably in this context. "Low risk" strains of HPV include those which are not associated or only weakly associated with increased risk of carcinoma in human subjects. Typically, the low-risk strains of HPV are the wart-forming strains, including HPV 6 and HPV 11.

The beads of the present invention are coupled to reactants which will specifically interact with a given analyte of interest within a sample. In one aspect, the reactants of the present invention are nucleic acids and the analytes within the sample which specifically react with the reactant are also nucleic acids.

Hence, this aspect of the subject invention uses primers which are directed to conserved regions of a strain of HPV but which flank strain-specific genomic sequences. The strain-specific sequences are referred to as "variable" sequences since they vary between strains compared to the conserved sequences which are constant between strains. Upon amplification, the amplicons are put into contact with subsets of beads in the beadset wherein each bead of each subset carries a capture nucleic acid primer or probe capable of hybridizing to the strain-specific amplicons. Multiplexing using bead size, fluorescence intensity and DNA binding specificity enables identification, sorting and distinguishing of HPV strains.

Accordingly, another aspect of the present invention contemplates a beadset for detecting one or more strains of HPV and/or for differentiating between two or more strains of HPV, wherein the beadset comprises a plurality of subsets of beads wherein:
(a) the beads of each subset are homogenous with respect to size;
(b) the beads within each subset are coupled to a nucleic acid capture probe which is capable of binding to a HPV strain-specific region of an HPV genome;
(c) the capture probe on each bead is labeled with the same label with each subset of beads having a different fluorescent intensity to create a heterogeneous mixture of beads based on fluorescent intensity; and
(d) at least two subsets of beads are mixed together to produce a beadset, wherein the subset identity and therefore the strain of HPV is identifiable by flow cytometry based on size, fluorescent intensity and sequence discrimination.

Still another aspect of the present invention contemplates a method for detecting and/or differentiating between two or more HPV strains in a sample, comprising the steps of:
(a) contacting the sample with a beadset comprising a plurality of subsets of beads wherein:
(i) the beads of each subset are homogenous with respect to size;
(ii) the beads within each subset are coupled to a nucleic acid capture probe which is capable of binding to a HPV strain-specific region of an HPV genome;
(iii) the capture probe on each bead is labeled with the same label with each subset of beads having a different fluorescent intensity to create a heterogeneous mixture of beads based on fluorescent intensity; and
(iv) at least two subsets of beads are mixed together to produce a beadset, wherein the subset identity and therefore the strain of HPV is identifiable by flow cytometry based on size, fluorescent intensity and sequence discrimination;
(b) incubating said beadset with said sample for a time and under conditions sufficient to allow said primers to bind to the HPV genome amplified to generate a replicon comprising a strain-specific region;
(c) detecting and/or differentiating the amplicons generated in the sample which are bound to said beads to thereby identify or distinguish between the two or more HPV strains.

The amplicons to which the nucleic acid capture probes are specific may also be labeled with a fluorescent reporter molecule.

Nucleic acids may be isolated from the subject sample using any method which is convenient with regard to the nature of the sample itself and the analyte. As used herein, the term "nucleic acid" refers to DNA and/or RNA. Typically, DNA is isolated, although under some circumstances which would be evident to one of skill in the art, it may be more preferable to isolate RNA, for example, when the analyte of interest is an RNA virus. If RNA is isolated, the RNA may be amplified, or the RNA may be reverse transcribed into cDNA using standard methods, for subsequent amplification and analysis.

Preferably, the "nucleic acid" is DNA. DNA may be isolated from the sample using any convenient means. For example, in the case of a virus such as HPV in a human cell sample, guanidine or a functionally equivalent agent may be used to lyse the cells. An exemplary guanidine-based method for cell lysis and DNA extraction is the method of Nelson and Krawetz (*Anal. Biochem.* 207(1):97-201, 1992). Guanidine-based lysis solutions are also commercially available from suppliers such as Qiagen, eg. QIAamp, PAXgene and the like. However, methods of lysis may change depending on the nature of the sample and analyte. For example, for the detection of an analyte in an environmental sample such as a soil or sediment sample, a glass-bead based cell lysis system may be more appropriate, such as the method of Kuske et al. (*Appl. Environ. Microbiol.* 64(7):2463-2472, 1998). In any event, the appropriate lysis protocol for a given analyte and sample would be readily determined by one of ordinary skill in the art with no undue experimentation.

After lysis of the cells, the DNA may be purified by any convenient means which would be readily evident to one of skill in the art (eg. see commercially available kits above). In a preferred embodiment of the invention, the DNA is purified using a limiting amount of a DNA binding agent such as, but not limited to, silica. By using a limiting amount of the DNA binding agent, a uniform amount of DNA may be isolated from different samples as the amount of DNA recovered in each case is equal to the maximum amount of DNA that can be bound by the limiting amount of DNA binding agent. The DNA bound to the DNA binding agent may then be recovered or eluted from the DNA binding agent using any convenient means.

Although DNA is a preferred nucleic acid, RNA may also be isolated from the sample using any standard RNA isolation protocol. RNA isolation typically involves a cell disruption step and an RNA isolation step. Exemplary cell disruption techniques which are suitable for the isolation of RNA include those presented in Ambion Technical Bulletin #183 (www.ambion.com/techlib/tb/tb_183.html). Furthermore, a range of exemplary RNA isolation kits which are suitable for a range of sample types are presented at www.ambion.com/techlib/basics/products/rnaisol_compchart.html. However, it should be understood that the present invention is not in any way limited by these specific methods and kits for RNA isolation and purification and the present invention is compatible with any. RNA isolation methods which would be evident to one of skill in the art.

The beadset may comprise, in relation to HPV detection as many subsets of beads as strains of HPV. Hence, the assay may employ 2, 3, 4, 5, 6, 7, 8, 9, 10, 11, 12, 13, 14, 15 or 16 subsets of beads each for HPV strains 6, 11, 16, 18, 31, 33, 35, 39, 45, 51, 52, 56, 58, 59, 66 and 68. Additional beads may also be used for controls. Suitable capture probes are disclosed in FIG. 9.

Hence, another aspect of the present invention is directed to a beadset for detecting one or more strains of HPV and/or for differentiating between two or more strains of HPV, wherein the beadset comprises a plurality of subsets of beads wherein:
(a) the beads of each subset are homogenous with respect to size;
(b) the beads within each subset are coupled to a nucleic acid capture probe selected from the list consisting of SEQ ID NOs: 5 through 20 which is capable of binding to a HPV strain-specific region of an HPV genome;
(c) the capture probe on each bead is labeled with the same label with each subset of beads having a different fluorescent intensity to create a heterogeneous mixture of beads based on fluorescent intensity; and
(d) at least two subsets of beads are mixed together to produce a beadset, wherein the subset identity and therefore the strain of HPV is identifiable by flow cytometry based on size, fluorescent intensity and sequence discrimination.

Still a further aspect of the present invention contemplates a method for detecting and/or differentiating between two or more HPV strains in a sample, comprising the steps of:
(a) contacting the sample with a beadset comprising a plurality of subsets of beads wherein:
(i) the beads of each subset are homogenous with respect to size; t
(ii) the beads within each subset are coupled to a nucleic acid capture probe is selected from the list consisting of SEQ ID NOs: 5 through 20 which is capable of binding to a HPV strain-specific region of an HPV genome;
(iii) the capture probe on each bead is labeled with the same label with each subset of beads having a different fluorescent intensity to create a heterogeneous mixture of beads based on fluorescent intensity; and
(iv) at least two subsets of beads are mixed together to produce a beadset, wherein the subset identity and therefore the strain of HPV is identifiable by flow cytometry based on size, fluorescent intensity and sequence discrimination;
(b) incubating said beadset with said sample for a time and under conditions sufficient to allow said probes to bind to the HPV genome amplified to generate a replicon comprising a strain-specific region;
(c) detecting and/or differentiating the amplicons generated in the sample which are bound to said beads to thereby identify or distinguish between the two or more HPV strains.

Accordingly, the beadsets may comprise in relation HPV 2, 3, 4, 5, 6, 7, 8, 10, 11, 12, 13, 14, 15, 16 subsets of beads each with one of a nucleic acid molecule selected from the listing consisting of SEQ ID NOs:5 through 20. Reference to these HPV strain-specific sequences in SEQ ID NOs:5 through 20 includes nucleic acid molecules having at least 90% identity to these sequences or capable of hybridizing thereto or their complementary forms under low stringency conditions. Reference to at least 90% includes 90, 91, 92, 93, 94, 95, 96, 97, 98, 99 and 100%.

The methods of the present invention rely, in part, on amplifying a nucleic acid from a sample using primers that bind to conserved sequences among different strains of the subject analyte, but which generate an amplicon which comprises a distinct nucleotide sequence for each strain of the analyte. In effect, the primers used in the present invention bind to sequences which are conserved among strains of the subject analyte which flank regions that are at least partially non-conserved or polymorphic between strains. Schematically, the amplified region in the analyte has the general structure of:

wherein:
C is a nucleotide sequence which is conserved among two or more strains of the analyte and is the binding site of the "forward" primer;
X is a nucleotide sequence, part or all of which comprises variation between different strains of the analyte;
C' is a nucleotide sequence which is conserved among two or more strains of the analyte and is the binding site of the "reverse" primer.

Amplification from primer sites such as those described above effectively allows the use of a "universal" primer set, which bind at C and C' to amplify X from a range of strains of the analyte. Furthermore, it should be noted that the amplicon amplified using the universal primers may comprise both conserved and variable regions.

In a preferred embodiment, primers are used which amplify HPV sequences. More preferably these primers are GP5+ is 5' TTTGTTACTGTGGTAGATACTAC 3' (SEQ ID NO:1) and GP6+ is 5' GAAAAATAAACTGTAAAT-CATATTC 3' (SEQ ID NO:2). These primers generate an amplicon from HPV which comprises both a conserved region (defined as Y in FIG. 3), and a region which is variable among different strains of HPV (defined as X in FIG. 3).

The present invention also contemplates the amplification of control sequences. In one embodiment, the control sequence may include a region of the genome of the subject from which a biological sample is derived. However, the present invention is not in any way limited to these particular control sequences and other control sequences which would be evident to one of skill in the art are also contemplated. Furthermore, the methods of the present invention may also be performed without the amplification of a control sequence.

In one preferred embodiment, the control sequence is amplified from the genome of a human subject using the primers LC1_F, which comprises the nucleotide sequence 5' TACACACAGGTGTACACAGA 3' (SEQ ID NO:3) and LC1_R which comprises the sequence 5' ACCAAGTACTC-TACGTGTTG 3' (SEQ ID NO:4).

Isolated DNA may be amplified using any DNA amplification protocol. A range of exemplary methods for the amplification of DNA which in no way limit the invention are presented in "*DNA Amplification: Current Technologies and Applications*" (Demidov and Broude Eds., Horizon Bioscience, 2004).

Isolated RNA may be amplified using any RNA methods known in the art and number of RNA amplification technologies have been developed. Two major categories of these are: (i) those that utilize thermal cycling such as RT-PCR and (ii) isothermal assays such as nucleic acid sequence-based amplification (NASBA) (Compton, *Nature* 350:91-92, 1991; Kievits et al., *J. Virol. Methods* 35:273-286, 1991) and transcription-mediated amplification (TMA) (Hill, *J. Clin. Ligand Assay* 19:43-51, 1996). Isothermal assays may be sub-divided, based on whether: (i) they copy and amplify the target sequence, such as TMA, NASBA and self-sustained sequence replication (3SR) (Guatelli et al., *Proc. Natl Acad. Sci. USA* 87:1874-1878, 1990; Chadwick et al., *J. Virol. Methods* 70:59-70, 1998; for review see Chan and Fox, *Rev. Med. Microbiol.* 10:185-196, 1999), or (ii) they generate a target-dependent signal which can be further amplified, e.g. invader assays (Lyamichev et al., *Nat. Biotechnol.* 17:292-296, 1999; Ryan et al., *Mol. Diagn.* 4:135-144, 1999). There are various other amplification technologies that do not fit readily into these categories, such as Q beta replicase (Lizardi et al., *Biotechnology* 6:1197-1202, 1988) and branched DNA (Todd et al., *J. AIDS Hum. Retrovirol.* 10:S35-S44, 1995; Pawlotsky et al., *J. Virol. Methods* 79:227-235, 1999). However, it should be understood that the present invention contemplates any method of RNA amplification that would be evident to one of skill in the art. Furthermore, it should be understood that the present invention also contemplates the use of reverse transcriptase or a functional equivalent thereof to convert RNA to DNA which may then be subsequently amplified.

In accordance with the present invention, the amplicons recited at steps (iii) and/or (iv) of the methods described supra are labeled. The amplicons of the present invention may be labeled using any convenient means. Exemplary methods include both pre- and post-synthesis methods. Pre-synthesis labeling methods include labeling of a PCR primer that is subsequently used for amplification of, and thereby incorporated into, an amplicon via PCR. In this method, the label is typically attached to the 5' end of a primer suitable for the amplification of the amplicon, although labeling at other positions within the primer, such as 3' labeling or non-terminal labeling, is also contemplated.

A chemical linker may also be used between the label and the polynucleotide which is labeled. Appropriate linker sequences will be readily ascertained by those of skill in the art, and are likely to include linkers such as C6, C7 and C12 amino modifiers and linkers comprising thiol groups. As will be readily ascertained, a primer may comprise the linker and label, or the linker alone, to which the label may be attached at a later stage.

Post-amplification labeling methods include nick-labeling systems wherein a labeled polynucleotide is synthesized from the amplicon using Klenow polymerase, or a functional equivalent thereof, from random primers. Labeled nucleotides, or nucleotides comprising a linker group, may be incorporated into the Klenow polymerase synthesized polynucleotide during synthesis.

In any event, other labeling methods should be readily evident to one of skill in the art and it should be understood that the present invention is in no way defined or limited by the choice of labeling method.

Preferably, the label used is a "fluorescent marker" or "fluorophore". Many different fluorescent markers will be familiar to those of skill in the art, and the choice of fluorescent marker in no way limits the invention. In a preferred embodiment of the present invention the fluorescent markers of the present invention comprise any fluorescent marker that can be attached to a polynucleotide and which is excitable using a light source selected from the group below:

(i) Argon ion lasers: comprise a blue, 488 nm line, which is suitable for the excitation of many dyes and fluorochromes that fluoresce in the green to red region. Tunable argon lasers are also available that emit at a range of wavelengths (458 nm, 488 nm, 496 nm, 515 nm and others).

(ii) Diode lasers: have an emission wavelength of 635 nm. Other diode lasers which are now available operate at 532 nm. Interestingly, this wavelength excites propidium iodide (PI) optimally. PI staining is widely used for DNA analysis, live/dead counting and ploidy determination. Blue diode lasers emitting light around 476 nm are also available (iii) HeNe gas lasers: operate with the red 633 nm line.

(iv) HeCd lasers: operate at 325 nm.

(v) 100 W mercury arc lamp: the most efficient light source for excitation of UV dyes like Hoechst and DAPI.

In more preferred embodiments of the present invention the fluorescent markers are selected from: hydroxycoumarin, aminocoumarin, methoxyciumarin, cascade blue, Lucifer yellow, NBD, Phyccerythrin (PE), PerCP, allophycocyanin, hoechst 33342, DAPI, SYTOX Blue, hoechst 33258, chromomycin A3, mithramycin, YOYO-1, SYTOX green, SYTOX orange, 7-AAD, acridine orange, TOTO-1, To-PRO-1, thiazole orange, TOTO-3, TO-PRO-3, LDS 751, Alexa Fluor dyes including Alexa Fluro-350, 430, 488, -532, -546, -555, -556, -594, -633, -647, -660, -680, -700 and -750; BoDipy dyes, including BoDipy 630/650 and BoDipy 650/665; CY dyes, particularly Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4', 5'-dichloro-2', 7'-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; TRITC, Tetramethylrhodamine (TMR); Carboxytetramethylrhodamine (TAMRA); Tetrachlorofluorescein (TET); Red 6B, FluorX, BODIPY-FL and Texas Red. In particularly preferred embodiments of the present invention, the marker is Cy5 which is particularly convenient for practice of the present invention.

However, in alternate embodiments of the invention, radioactive or non-radioactive labels may be used to label the amplicon. Convenient radioactive labels include $^{32}$P and $^{3}$H. These labels may be incorporated into the amplicon and/or primer using any convenient means. A range of non-radioactive labeling methods may also be used. Exemplary non-radioactive labeling methods which in no way limit the present invention are presented in Speel (*Histochem. Cell Biol.* 112:89-113, 1999).

The term "reactant" as used herein should be understood to comprise a polynucleotide immobilized to a bead. More particularly, each reactant comprises a polynucleotide comprising a sequence which is complementary to an amplicon generated according to the methods described herein, which is bound or otherwise associated with a physiochemically distinguishable bead. A reactant may also comprise a sequence which is complementary to a control sequence as hereinbefore defined, ie. a sequence amplified from the genome of a multicellular organism (Z) or the amplicon of a nucleotide sequence which is conserved among strains of the analyte (Y).

Accordingly, a beadset of reactants may comprise:

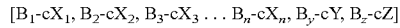

wherein:

$B_1 \ldots B_n, B_y, B_z$ are each physiochemically distinguishable beads;

$cX_n$ is a polynucleotide immobilized to a bead wherein said polynucleotide comprises a nucleotide sequence which is complementary to a particular nucleic acid sequence which is specific to an analyte or a particular strain of a subject analyte and wherein n is the number of analytes or particular strains of a subject analyte to be detected using the beadset;

cY is an optional member of the beadset and is a polynucleotide immobilized to a bead wherein said polynucleotide comprises a nucleotide sequence which is complementary to a sequence which is conserved among the analytes or strains of a subject analyte;

cZ is an optional member of the beadset and is a polynucleotide immobilized to a bead wherein said polynucleotide comprises a nucleotide sequence which is complementary to a control sequence which is amplified from a multicellular subject.

Preferably, the subject analyte is HPV and the control DNA sequence is a human genomic DNA sequence.

By "complementary", it is to be understood that the immobilized polynucleotide of the reactant should hybridize to an amplicon generated according to the methods described herein under low stringency conditions. Preferably the immobilized polynucleotide should bind to the sample and standard under medium stringency conditions, and most preferable the immobilized polynucleotide should bind to the sample and standard under high stringency conditions.

Reference herein to low stringency includes and encompasses from at least about 0 to at least about 15% v/v formamide (including 1%, 2%, 3%, 4%, 5%, 6%, 7%, 8%, 9%, 10% 11%, 12%, 13% and 14% v/v formamide) and from at least about 1 M to at least about 2 M salt for hybridization, and at least about 1 M to at least about 2 M salt for washing conditions. Generally; low stringency is at from about 25-30° C. to about 52° C., such as 25, 26, 27, 28, 29, 30, 31, 32, 33, 34, 35, 36, 37, 38, 39, 40, 41, 42, 43, 44, 45, 46, 47, 48, 49, 50, 51 and 52° C. The temperature may be altered and higher temperatures used to replace formnamide and/or to give alternative stringency conditions. Alternative stringency conditions may be applied where necessary, such as medium stringency, which includes and encompasses from at least about 16% v/v to at least about 30% v/v formamide, including 16%, 17%, 18%, 19%, 20%, 21%, 22%, 23%, 24%, 24%, 26%, 27%, 28%, 29% and 30% v/v formamide, and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5:109, 1962). However, the $T_m$ of a duplex DNA decreases by 1° C. with every increase of 1% in the number of mismatch base pairs (Bonner and Laskey, *Eur. J. Biochem.* 46:83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The beads, $B_1 \ldots B_n$, $B_y$, $B_z$, of the reactant beadsets are each physiochemically distinguishable beads. The term "physiochemically distinguishable" refers to any physical or chemical characteristic which allows one bead, eg. $B_1$ to be differentiated from another bead eg. $B_2$. Accordingly, the physiochemically distinguishable beads allow differentiation of particular reactants.

In a preferred embodiment the bead comprises a "microparticle". As will be evident to those of skill in the art, almost any material, homogenous or otherwise may be used for the microparticle. The microparticles contemplated herein may also comprise more than one substance, and as such may comprise shells, alloys or mixtures of organic and/or inorganic substances. Particularly useful materials which may be used in accordance with the present invention and which represent preferred embodiments of the present invention include materials selected from the list consisting of: silica (for example: quartz or glass), latex, titania, tin dioxide, yttria, alumina, and other binary metal oxides (such as ZnO), perovskites and other piezoelectric metal oxides (such as $BaTiO_3$), ZnS, sucrose, agarose and other polymeric beads. In a particularly preferred embodiment, the microparticle comprises silica.

In a preferred embodiment, the term "physiochemically distinguishable" refers to a measurable difference in any of bead size, the presence or absence of a particular optically detectable label and/or the intensity of an optically detectable label.

Bead contemplated by the present invention may be produced in any convenient regular or irregular 3-dimensional shape. However, it is generally practical to synthesize small spheres or spheroidal particles. Such spheres or spheroidal particles are also referred to herein as "beads". Accordingly, in preferred embodiments of the present invention, the "microparticles" of the present invention are substantially spherical or spheroidal or comprise a "microsphere".

Although the beads of the present invention may be referred to as "microspheres" the actual size of the particles depends on a variety of factors and the particles may or may not actually comprise measurements in the micrometer range. In one preferred embodiment the bead comprises a diameter (or equivalent measurement in a non-spheroidal particle) of about 300 nm to about 30 μm, including 300 nm, 350 nm, 400 nm, 450 nm, 500 nm, 550 nm, 600 nm, 650 nm, 700 nm, 750 nm, 800 nm, 850 nm, 900 nm, 950 nm, 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, 5.0 µm, 5.1 µm, 5.2 µm, 5.3 µm, 5.4 µm, 5.5 µm, 5.6 µm, 5.7 µm, 5.8 µm, 5.9 µm, 6.0 µm, 6.1 µm, 6.2 µm, 6.3 µm, 6.4 µm, 6.5 µm, 6.6 µm, 6.7 µm, 6.8 µm, 6.9 µm, 7.0 µm, 7.1 µm, 7.2 µm, 7.3 µm, 7.4 µm, 7.5 µm, 7.6 µm, 7.7 µm, 7.8 µm, 7.9 µm, 8.0 µm, 8.1 µm, 8.2 µm, 8.3 µm, 8.4 µm, 8.5 µm, 8.6 µm, 8.7 µm, 8.8 µm, 8.9 µm, 9.0 µm, 9.1 µm, 9.2 µm, 9.3 µm, 9.4 µm, 9.5 µm, 9.6 µm, 9.7 µm, 9.8 µm, 9.9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm. More preferably, the bead comprises a diameter (or equivalent measurement in a non-spheroidal particle) of between 1 µm and 10 µm.

In one particularly preferred embodiment, the beads are AmpaSand (Trade mark: Genera Biosystems) beads produced by Genera Biosystems. These beads are commercially available and are described at www.generabiosystems.com/generabiosystems/technology/AmpaSandBeads/. However, the present invention should not be considered in any way limited to the use of these beads specifically.

The beads may be distinguished on the basis of the presence or absence of one or more "optically detectable labels". Typically, a particular bead may comprise 0, 1, 2, 3, 4, 5 optically detectable labels. As used herein, the term "optically detectable label" refers to any molecule, atom or ion which emits fluorescence, phosphorescence and/or incandescence. Convenient optically detectable labels include those which emit in the ultraviolet (wavelength range of about 350 nm to about 3 nm), visible (wavelength range of about 350 nm to about 800 nm, near infrared (NIR) (wavelength range of about 800 nm to about 1500 nm) and/or infrared (IR) (wavelength range of about 1500 nm to about 10 m) ranges. However, due to the ease of detection, in one particularly preferred embodiment, the optically detectable label is detectable in the visible wavelength range.

In further preferred embodiments of the subject invention, the optically detectable label comprises one or more labels selected from the list consisting of: a fluorophore, a semiconductor particle, phosphor particle, a doped particle, or a nanocrystal or quantum dot.

In one particularly preferred embodiment of the present invention, the optically detectable label is a fluorophore. As used herein, the term "fluorophore" refers to any molecule which exhibits the property of fluorescence. For the purposes herein, the term "fluorescence" may be defined as the property of a molecule to absorb light of a particular wavelength and re-emit light of a longer wavelength. The wavelength change relates to an energy loss that takes place in the process. The term "fluorophore" may encompass a range of optically detectable labels such as chemical fluorophores and dyes as well as quantum dots.

One particularly convenient optically detectable label which may be used in accordance with the present invention is to embed fluorescent particles of semiconductors. These optically detectable label particles may be so small that their properties and emission become size dependent. Such small optically detectable label particles are referred to in the art as semiconductor nanoparticles, quantum dots, quantum wires, quantum rods or nanocrystals or Q-particles. However, as used herein, the term "Quantum Dot" or "QD" is to be understood to encompass all such particles. Furthermore, optically detectable labels comprising QDs may comprise approximately spherical or spheroidal particles, or coated spherical or spheroidal particles. However, the term QD should not be considered in any way to be limited to a spherical, spheroidal, circular, cylindrical or any other morphology of a "dot". For example, as used herein QDs may also comprise other morphologies including, inter alia, rod-like, ellipsoidal, or coated rod-like or ellipsoidal particles.

QDs consist of a nanometer-scale crystalline core of semiconductor material; biologically active versions are typically surrounded by a protective shell and external coat. For example, QDs may comprise semiconductor crystallites which are about 2 nm to about 30 nm in diameter and may contain approximately 50-500,000 atoms within the crystal, including luminescent crystals comprising materials such as ZnS, ZnSe, ZnTe, CdS, CdSe, CdTe, PbS, PbSe, PbTe, HgS, HgSe, HgTe, Si, ZnO.

QDs fluoresce with a broad absorption spectrum and a narrow emission spectrum. Unlike some other fluorophores, which have distinct absorption spectra, QDs absorb light over a wide spectral range, which allows quantum dots to be excited with a range of light sources, such as lasers, arc lamps, or LEDs. Furthermore, a collection of different QDs can be used in multiplex applications using only a single excitation source. However, the emission spectra for each dot is typically very narrow, in the order of about 30 nm, the exact color depending on the particle's diameter and composition. Furthermore, the narrow emission spectrum of QDs permits spectral resolution of adjacent dots. In addition to the benefits above, QDs are also relatively photostable, even during intense excitation, and are brighter than fluorophores.

In light of the foregoing, it should also be understood that the present invention encompasses the use of different sized QDs.

Furthermore, the present invention contemplates QDs which are treated with procedures such as thermal treatment, surface modification, alloying, surface passivation or capping with surface coatings to enable the QD to emit with high quantum yield and to improve the photostability for long periods of time.

QDs are also commercially available from companies such as Quantum Dot Corp. (QDC), which produces QDs such as the Qdot [Trade Mark] 605 streptavidin conjugate, containing a cadmium-selenide core that emits at 605 nm. Qdot conjugates that emit at 525, 565, 585, and 655 nm are also available. However, it should be understood that the present invention is not limited in any way by the particular composition of the QD (or any other optically detectable label) and any QD (commercial or otherwise) may be compatible with the present invention.

There are also many fluorescent dyes that are available in the art which may be used as fluorophores in accordance with the present invention. An important property of a fluorescent dye or other fluorophore, which determines it's potential for use is the excitation wavelength of the fluorophore; it must match the available wavelengths of the light source. However, many different fluorescent dyes and other fluorophores will be familiar to those of skill in the art, and the choice of fluorescent marker in no way limits the subject invention. Particularly convenient fluorescent dyes which may be used for the labeling of a substrate include those discussed supra with regard to labeling of the PCR amplicon. However, when choosing fluorescent labels, the emission spectra of the fluorescent label used for the binding agent(s) should be distinct from the emission spectrum of the label used for the amplicon(s).

Two dyeing techniques are commonly used to fluorescently label beads and microspheres—internal dyeing and external dyeing (surface-labeling). The two techniques produce beads with unique properties, each beneficial for different applications. Internal dyeing produces extremely stable particles with typically narrow fluorescence emissions. These beads often display a greater resistance to photobleaching. As the fluorophore is inside the beads, surface groups are available for use in conjugating ligands (proteins, antibodies, nucleic acids, etc.) to the surface of the bead. For this reason, internally labeled beads are typically used in analyte-detection and immunoassay applications. Surface-labeling involves conjugation of the fluorophore to the bead surface. Because the fluorophores are on the surface of the bead, they are able to interact with their environment just as the fluorophores on a stained cell. The result is a bead standard that exhibits the same excitation and emission properties as stained cell samples, under a variety of different conditions, such as the presence of contaminants or changes in pH. The "environmentally responsive" nature of surface-labeled beads makes them ideally suited for mimicking biological samples. Externally labeled beads are frequently used as controls and standards in a number of applications utilizing fluorescence detection. However, the present invention contemplates the association of a bead with a fluorescent label via any means.

The terms "phosphorescent beads", "phosphor beads" and "phosphors" are used interchangeably herein. What constitutes a phosphorescent optically detectable label would be readily understood by one of skill in the art. However, by way of example, which in no way limits the invention, suitable phosphors include small particles of ZnS, ZnS:Cu, Eu oxide and other phosphors used in display devices.

A optically detectable label comprising a "doped bead" may include a particle which comprises occluded amounts of one or more rare earth ions, such as Eu, Y, Yb, Sm and the like.

As used herein, the term "optically detectable label" should be understood to also encompass multiple optically detectable labels, mixtures of optically detectable labels, coated nanocrystals, alloys and other complex mixtures that would be evident to the skilled artisan. The use of all such optically detectable labels is to be considered as being within the scope of the methods and agents described herein.

Furthermore, the optically detectable label of the reactant may comprise an optically detectable label incorporated into the immobilized polynucleotide sequence which is bound or otherwise associated with the bead, rather than being a label directly associated with the bead per se.

The beads are generally labeled by the immobilized "tag" or probe oligonucleotide. This tag carries an internal amine (NH2) which is then modified by conjugation with a succinimidyl ester of a dye. In the current set, the dye used is BODIPY-TMR. By mixing labelled and unlabelled tags and then conjugating this mix to the beads, one can produce classes of beads with different levels of the fluorescent marker. The ratios conveniently used are in a series of $1:5^x$; that is, the different classes are produced by using the ratio of unlabeled:labeled tags. This is generically exemplified below in Table 4.

TABLE 4

| Ratio of unlabeled:labeled tags | | |
| --- | --- | --- |
| Class | Rel amount Unlabeled | Rel Amt Labeled |
| All | 0 | All |
| None | All | 0 |

TABLE 4-continued

| Ratio of unlabeled:labeled tags | | |
| --- | --- | --- |
| Class | Rel amount Unlabeled | Rel Amt Labeled |
| 1/5 | 5 | 1 |
| 1/25 | 25 | 1 |
| 1/125 | 125 | 1 |

The optically detectable label may be applied to a bead at a range of concentrations or intensities, thereby providing another basis on which particular beads may be "physiochemically distinguishable". For example, if the maximum detectable intensity of the signal of a particular optically detectable is deemed to be 100%, the label may be applied to a range of beads to give intensities of 0%, 2%, 4%, 6%, 8%, 10%, 15%, 20%, 25%, 30%, 35%, 40%, 45%, 50%, 60%, 70%, 80%, 90%, 100%.

In a particularly preferred embodiment, the beadset of reactants comprises beads of 3.0 µm, 3.5 µm, 4.1 µm, 5.0 µm, 5.6 µm and 6.8 µm wherein the 3.0 µm, 3.5 µm and 4.1 µm diameter beads are labeled at 0% and 100%, the 5.0 µm diameter beads are labeled at 0%, 100% and 20% and the 5.6 µm and 6.8 µm diameter beads are labeled at 0%, 100%, 20% and 4%.

The immobilized polynucleotide component of the reactant, eg. $cX_n$, cY and/or cZ may be bound to a bead using any convenient means.

The immobilized polynucleotide may be encapsulated in beads during their production or may be attached to their surface post-production. The choice method used to associate the polynucleotide with the bead will depend on the material used, as would be readily ascertained by the skilled artisan. In addition, further treatments, including silanization (coating of the substrate with silanes), may be performed on the beads prior to attachment of the polynucleotide in order to increase the binding of said polynucleotide to the bead.

Generally, beads may be coated with any compound that will covalently attach, or otherwise adsorb, to the surface of the bead, and in addition the reactant should also have a chemical moiety for the attachment of a polynucleotide, such as a thiol, amine or carboxyl group. Examples of compounds with these characteristics include amino-terminated silanes such as amino-propyltrimethoxysilane or amino-propyltriethoxysilane. In addition to silanes, compounds such as poly-L-lysine that non-covalently attach to the glass surface and electrostatically adsorb the phosphate groups of the polynucleotide are also within the scope of the present invention. Therefore, other compounds, including other silanes suitable for the attachment of a polynucleotide to a surface would be readily identified by the skilled artisan, and the present invention is not limited by the choice of compound.

The polynucleotide can be attached to the bead using any convenient means, typically this is done by physical adsorption or chemical linking. In addition, beads may be further coated with an agent that promotes or increases the adsorption or binding of the polynucleotide to the surface of the bead, such as amino-silanes. However, other agents that perform this function will be readily identified by persons of skill in the art.

In one embodiment, the nucleic acid molecule is bound to the bead via the Universal Anchoring System (UAS) (Trade mark: Genera Biosystems). Briefly, this system involves the use of a "bridge" nucleic acid molecule to ligate a nucleic acid "tag" sequence on the substrate with a target sequence. The "bridge" sequence is partially complementary to the tag sequence and partially complementary to the target sequence, such that the bridge sequence may bind to both the tag and target sequences and hold them in alignment such that the tag and target sequences may be ligated using a ligase. The UAS is also commercially available and is described in detail at www.generabiosystems.com/generabiosystems/technology/UAS/. However, the present invention should not be considered in any way limited to this particular method of linking a nucleic acid molecule to a substrate.

Determination of whether binding has occurred between an amplicon and a reactant may be done using any methodology which allows localization of a bound amplicon label to a particular physiochemically distinguishable reactant. In a particularly preferred embodiment, flow cytometry is used.

Flow Cytometry may be defined as a technology to measure properties of particles or cells as they move, or flow, in liquid suspension. An analogy may be made with a more familiar item of laboratory equipment, the microscope, to further describe this technology. Most microscopes have the following components:

A Light Source

The typical microscope uses a light bulb to illuminate the object. In the flow cytometer, the light source is often a laser. Lasers are used because they provide a very concentrated and intense beam of monochromatic light. The monochromatic character of the light is especially important in making fluorescence measurements.

The Stage

In a microscope, the stage is movable to allow passage of the object to the viewing field of an objective lens. In the flow cytometer, the cells or particles exist in liquid suspension. The liquid flows in response to air pressure, past an objective lens, thus carrying the cells or particles through the viewing field.

The Lens

In both the microscope and the flow cytometer, the lens collects light from the object.

The Filters

Some microscopes have filters to select those characteristics of the light that are most important to the observer. This is particularly true of fluorescence microscopes. In fluorescence, dye molecules are excited by light of a characteristic wavelength which then produce emitted light of a longer wavelength. The filters remove the excitation light to allow the emission light to be seen or measured.

The Detectors

In a microscope, the light detector is the observer. The flow cytometer uses highly sensitive light detectors called photomultiplier tubes (PMT's). The detectors must be able to measure the brief flashes of emitted light from cells or particles that are moving one at a time through the viewing field of the objective lens at rates of up to several thousand per second.

Most flow cytometers can measure both Light Scatter and Fluorescence.

FIG. 1 shows the major components of one particular model of flow cytometer. One tank in the bottom supplies a buffer which carries the cells or particles through the instrument, while a second tank collects all of the waste fluid. The purpose of the carrier fluid (usually called sheath fluid) is to draw the suspension out so that the cells or particles pass in single file through the laser beam.

The laser at the left, front, illuminates the cells or particles flowing upward from the test tube with a blue beam. Forward light scatter is collected by a lens in-line with the laser beam (the laser beam itself is blocked by a small opaque bar) and reflected onto a light detector. Side light scatter and fluorescence is collected by a lens located at a right angle to the laser beam. The illustrated instrument can measure three colors of fluorescence in the green, orange, and red regions of the spectrum. The colors are separated by filters that either reflect or transmit only the desired wavelengths to the appropriate detectors.

Finally, all the electronic signals from the detectors are passed over to a computer (not shown) which records them and displays results. Since all measurements are made on each cell simultaneously, correlations between them can be determined. Also, one measurement may be used to select a subset of cells for study using another measurement. For example, it is possible to examine both fluorescence and particle size.

In a preferred embodiment, beads are detected and/or sorted according to the method of the present invention using flow cytometry. The present invention, however, is in no way limited to the particular flow cytometry method or apparatus hereinbefore described. This example was provided only for illustrative purposes, and the present invention is not to be limited to an instrument or method according to the example provided.

Using flow cytometry, the size of a given bead may be determined by the light scatter of the object.

Light scatter is the interaction of light and matter. All materials, including beads, will scatter light. It is composed largely of light that is reflected or refracted. The position from which an object is viewed often determines what can be told about it. In the flow cytometer, light scatter detectors are usually located opposite the laser (relative to the cell or particle), and to one side of the laser, in-line with the fluid-flow/laser beam intersection. The measurements made by these detectors are called forward light scatter and side light scatter, respectively.

Forward light scatter provides some information on the relative size of individual cells or particles, whereas side light scatter provides some information on the relative granularity of individual beads. They are often used in combination to distinguish the different major categories of white cells in unseparated mammalian blood, but are useful in a wide variety of other assays as well, such as the determination of the size of a microparticle.

The present inventors have determined that flow cytometry is able to distinguish between beads of about 3.0 μm, about 3.5 μm, about 4.1 μm, about 5.0 μm, about 5.6 μm and about 6.8 μm in diameter. Other bead classes can also be distinguished, such as between 5.0 and 5.6 and 5.6 and 6.8. Accordingly, the present inventors have identified that flow cytometry can differentiate up to at least 6 different sizes of beads.

In addition to size detection, flow cytometers typically have one or more lasers and detectors for the detection of fluorescence in a sample. Fluorescence is the property of a molecule to absorb light of a particular wavelength and re-emit light of a longer wavelength. The wavelength change relates to an energy loss that takes place in the process. It is a characteristic that makes fluorescence extremely useful: filters may be used to exclude the excitation light from the light detector or the viewer. Thus, the only light measured or seen originates from the fluorophore. Interference from background or stray light striking the detectors is extremely low.

There are many fluorescent dyes that are useful for flow cytometry. They bind to a variety of cytochemical components, such as nucleic acids; proteins; specific cell-membrane, nuclear, and cytoplasmic receptors; intracellular ion molecules; and many more. A key property of a fluorescent dye which determines it's potential for use in a flow cytometric assay is the excitation wavelength, ie. it must match the available wavelengths of the light source.

In another aspect, the present invention provides a method for diagnosing an infection by a pathogenic analyte in a subject, said method comprising:
 (i) obtaining a biological sample from the subject which putatively comprises said pathogenic analyte;
 (ii) isolating nucleic acid from said sample;
 (iii) amplifying the nucleic acid from said sample using primers which generate an amplicon which is distinct for said analyte or a particular strain of said analyte;
 (iv) optionally amplifying a control nucleic acid sequence from the subject;
 (v) optionally effecting labeling of the amplicon(s) recited at steps (iii) and/or (iv);
 (vi) hybridizing the labeled amplicon(s) to a beadset of reactants wherein each member of the beadset comprises a nucleic acid molecule having complementarity to a nucleotide sequence of the analyte or a particular strain of the analyte, bound or otherwise associated with a physiochemically distinguishable bead; and
 (vii) determining to which of the reactants an amplicon has bound;
wherein the association of an amplicon with a particular reactant is indicative of an infection by the analyte in the subject.

As used herein the term "subject" refers to any organism may be susceptible to infection by another analyte. As such, a "subject" includes, but is not limited to animals, plants, fungi and bacteria (which may be infected by bacteriophage). As used herein the term "animal" preferably includes a mammal and more preferably a primate including a lower primate and even more preferably, a human. However, the term "animal" also specifically includes livestock species such as cattle, horses, sheep, pigs, goats and donkeys as well as laboratory animals. Examples of laboratory test animals include mice, rats, rabbits, guinea pigs and hamsters. Rabbits and rodent animals, such as rats and mice, provide a convenient test system or animal model as do primates and lower primates. Non-mammalian animals such as avian species, zebrafish, amphibians (including cane toads) and *Drosophila* species such as *Drosophila melanogaster* are also contemplated.

The "subject" may also be a non-animal such as a plant. The term "plant" specifically includes plants of agricultural value such as cereal plants (eg. wheat, barley, oats, rye, triticale and maize), rice, fruit trees (eg. apples, bananas, mangoes and oranges), sugarcane, horticultural crop plants (eg. potatoes, carrots and onions) and the like.

However, in one preferred embodiment, the present invention provides a method for diagnosing HPV infection in a human subject, said method comprising:
 (i) obtaining a biological sample from the human subject which putatively comprises HPV;
 (ii) isolating nucleic acid from said sample;
 (iii) amplifying the nucleic acid from said sample using primers which generate an amplicon which is distinct for said analyte or a particular strain of said analyte;
 (iv) optionally amplifying a control nucleic acid sequence from the genomic DNA of the human subject;
 (v) optionally effecting labeling of the amplicon(s) recited at steps (iii) and/or (iv);
 (vi) hybridizing the labeled amplicon(s) to a beadset of reactants wherein each member of the beadset comprises a nucleic acid molecule having complementarity to a nucleotide sequence of HPV or a particular strain of HPV, bound or otherwise associated with a physiochemically distinguishable substrate; and
 (vii) determining to which of the reactants an amplicon has bound;
wherein the association of an amplicon with a particular reactant is indicative of HPV infection in the human subject.

In a related aspect, the present invention also contemplates a method for determining the risk of a human subject developing a disease associated with one or more strains of HPV said method comprising:
 (i) obtaining a biological sample from the human subject which putatively comprises HPV;
 (ii) isolating nucleic acid from said sample;
 (iii) amplifying the nucleic acid from said sample using primers which generate an amplicon which is distinct for said analyte or a particular strain of said analyte;
 (iv) optionally amplifying a control nucleic acid sequence from the genomic DNA of the human subject;
 (v) optionally effecting labeling of the amplicon(s) recited at steps (iii) and/or (iv);
 (vi) hybridizing the labeled amplicon(s) to a beadset of reactants wherein each member of the beadset comprises a nucleic acid molecule having complementarity to a nucleotide sequence of HPV or a particular strain of HPV, bound or otherwise associated with a physiochemically distinguishable substrate; and
 (vii) determining to which of the reactant an amplicon has bound;
wherein the association of an amplicon with a particular reactant comprising a polynucleotide which is complementary to a strain of HPV associated with a particular disease, is indicative of an increased risk said disease in the subject.

The labeling of the amplicons are as outline in part (v) is preferred. Hence, both the amplicons and the beads are labeled.

Exemplary diseases associated with one or more particular strains of HPV include those presented in Table 3. Accordingly, in this aspect, the present invention provides a method for diagnosing an increased risk of a subject developing a particular disease by specifically identifying which strain of HPV is infecting the subject. In a particularly preferred embodiment, the method is adapted to determining the risk of a human subject developing cervical cancer.

The present invention further contemplates a diagnostic kit for use according to the methods described herein, including diagnosing HPV infection in a human subject and/or assessing the risk of a human subject developing an HPV-associated disease, including cervical cancer. The kit comprises a beadset of reactants which each comprise a polynucleotide which is complementary to a nucleotide sequence of a particular strain of HPV, bound or otherwise associated with a physiochemically distinguishable substrate. Optionally, the kit may also comprise primers bind to conserved sequences among different strains of HPV, but generate an amplicon which comprises distinct nucleotide sequence for each strain of HPV wherein the amplicon generated is putatively complementary to a polynucleotide bound to or otherwise associated with one or more physiochemically distinguishable beads of the kit.

In one preferred embodiment, the beadset of reactants comprises at least group of beads, each comprising a diameter of any one of about 3.0 µm, about 3.5 µm, about 4.1 µM, about 5.0 µm, about 5.6 µm and about 6.8 µm. In a further preferred embodiment, each size group of beads comprises one or more sub-groups of microspheres each with a fluorescent label at a range of different intensities. More preferably, the fluorescent label is TMR and is applied at intensities of about 0%, about 4%, about 20% and about 100%.

In a futher preferred embodiment, the kit comprises the primers GP5+ and GP6+ and optionally primers LC1_F and LC1_R.

The kit may also be in the form of a solid phase chip or support, commonly referred to as a biochip. All or part of the reagents used in the subject assay may be incorporated into a biochip or miniaturized into a nanoassay. Although flow cytometry is particularly useful in measuring outputs of the subject assay, the biochip can be used to measure or automate other signals such as those associated with whispering gallery mode assays.

Notwithstanding fluorescent intensities is a preferred aspect of the multiplexing method, other forms of identification are encompassed by the present invention. One such alternative method includes whispering gallery mode (WGM) detection. In this embodiment, a fluorescent marker is incorporated into beads of a subset or incorporated or bonded to DNA on the surface of the beads. This fluorescent marker can excite the WGMs with a laser or unfocussed white light source or with filtered unfocussed white light source.

WGMs allow only certain wavelengths of light to be emitted from the particle. The result of this phenomenon is that the usual broad emission (10-100 nm wide) bands from, for example, a fluorophore become constrained and appear as a series of sharp peaks corresponding effectively to standing mode patterns of light within the particle. In accordance with the present invention, it has been determined that the WGM profile is extremely sensitive to changes at the surface of the microspheroidal particle and that the WGM profile changes when the microspheroidal particle interacts with analytes or molecules within its environment.

Accordingly, another aspect of the present invention contemplates a method of detecting an analyte such as an amplicon from an HPV strain comprising a strain-specific sequence, said method comprising contacting at least one set of microspheroidal particles with a sample putatively comprising said analyte, wherein each particle within a set of microspheroidal particles comprises an optically detectable label and an immobilized putative binding partner of said analyte (e.g. a primer or probe capable of binding, capturing or otherwise immobilizing an amplicon from an HPV strain) wherein each particle set has a defined WGM profile, wherein binding of said analyte to said immobilized binding partner results in a change in said WGM profile of said at least one set of microspheroidal particles which is indicative of the presence of said analyte.

The methods of the present invention may be applied to detect modulation in the WGM profile of a microspheroidal particle wherein said modulation results from detection of binding or other association of molecules in a sample to potential binding particles immobilized to the surface of the microspheroidal particle. Detection of binding reactions between an analyte and its binding partner based on sensitive changes in WGM profiles enables the identification and isolation of the analytes.

A feature of the present invention is that the microspheroidal particles may be excited with a wide range of light sources, facilitating measurement in many different WGM profiles.

An "optically detectable label" may be any molecule, atom or ion which emits fluorescence, phosphorescence and/or incandescence. In one preferred embodiment of the present invention, the optically detectable label is a fluorophore, which may encompass a range of optically detectable labels such as chemical fluorophores and dyes as well as quantum dots.

In one specific embodiment, the present invention provides a microspheroidal particle comprising a latex or silica particle which is 1 µm to 100 µm in diameter, labeled with an optically detectable label, such as a fluorophore or quantum dot, the particle further comprising a putative binding partner of an analyte to be detected. An example is a capture nucleic acid molecule capable of binding to an HPV amplicon generated by the amplification using two primers to a conserved region of the HPV genome which flank a strain-specific region. The optically detectable label is detectable at visible wavelengths and the microspheroidal particle exhibits one or more WGM profiles. One or more of the WGM profiles of the microspheroidal particle detectably modulates when analytes interacts with the immobilized binding partner on the particle. Any such change in WGM profile is indicative of the presence of an analyte which has bound to its binding partner.

The present invention is further described by the following non-limiting examples:

EXAMPLE 1

HPV Diagnosis—DNA Isolation and Amplification

Figure 2:
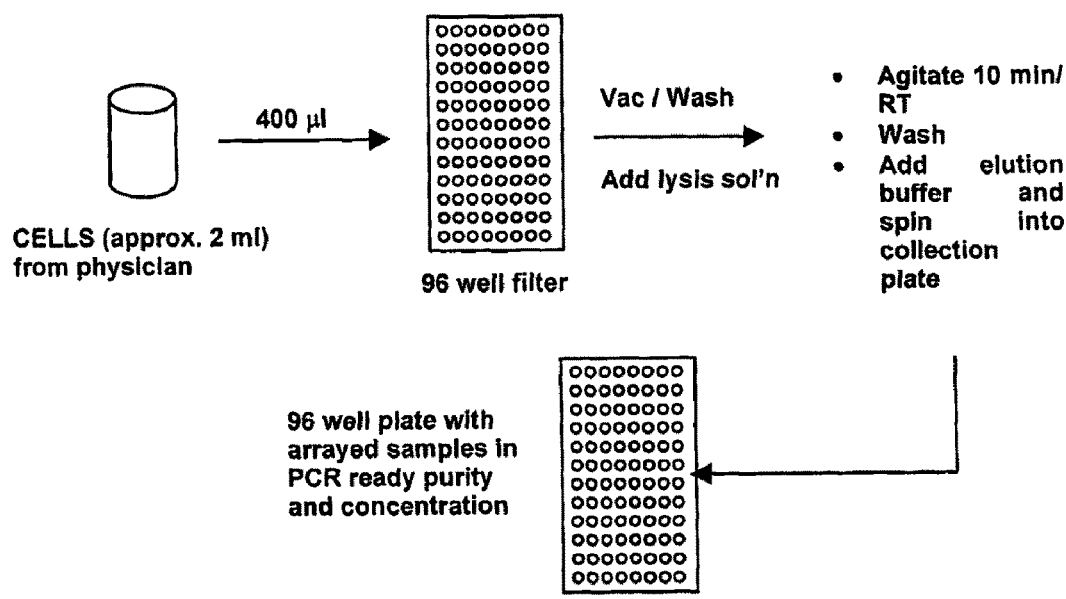
FIG. 2 is a graphical representation showing a schematic of the DNA extraction protocol used in the HPV diagnostic method.

An overview of the DNA extraction protocol used to isolate DNA for the HPV diagnostic method is shown in FIG. 2.

Figure 3:
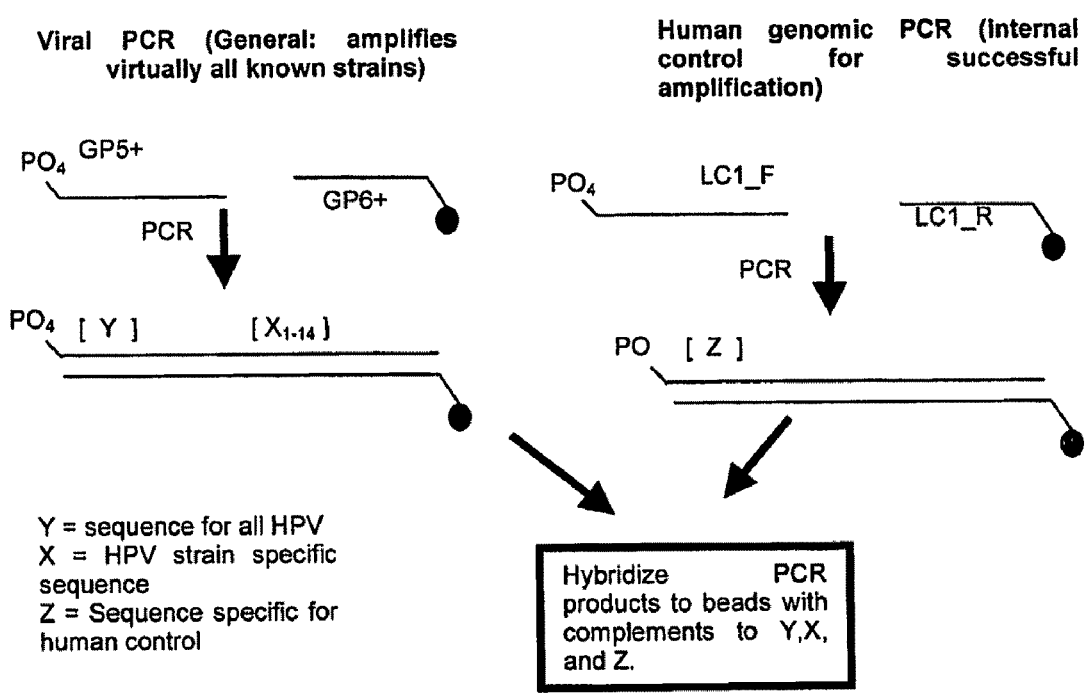
FIG. 3 is a graphical representation showing the PCR protocol used to amplify HPV and human DNA from a DNA sample. GP5+ and GP6+ refer to universal HPV primers which bind to conserved sequences (Y) in HPV and generate an amplicon which comprises a region which is variable between HPV strains ($X_{1-16}$). Primers LC1_F and LC1_R amplify a human genomic DNA region (Z) which serves as a control in the later hybridization steps. Primers GP6+ and LC1_R comprise a fluorescent label which is incorporated into the amplicon generated.

As shown in FIG. 3, PCR was used to amplify the DNA sample. The primers GP5+ and GP6+ were used to generate an amplicon for any HPV strain which was present in the DNA sample. Primer GP6+ comprised a fluorescent label, specifically Cy5 to allow later visualization of the amplicon binding to the binding agents. The viral amplicons generated comprised both a conserved region (Y) which is conserved among all the strains of HPV examined and a region which is variable (i.e. strain-specific) between HPV strains, $X_n$, wherein n represents a variable region associated with each HPV strain. The immobilized binding partners on beads specifically bind to the HPV strain-specific genome.

Also, an amplicon from the human subject genomic DNA was also generated using the LC1_F and LC1_R primers to serve as a control. In this case, primer LC1_R also carried a Cy5 label.

EXAMPLE 2

HPV Diagnosis—Multiplex Detection

The amplicons generated in Example 1 were hybridized to an array of binding agents, each carrying a polynucleotide which is complementary to the variable region of the putative viral amplicon generated from each of HPV strains c, 11, 16, 18, 31, 33, 35, 42, 45, 51, 52, 56, 58, 59, 67 and 68 ($X_1$ through $X_{16}$). See FIG. 9 for the nucleotide sequences of the capture nucleic acids immobilized to the beads. Furthermore, the array comprises a binding agent which comprises a polynucleotide which is complementary to conserved region of the HPV viral amplicons (Y). Finally, a binding agent comprising a polynucleotide which is complementary to the sequence of the human control amplicon is included. The capture nucleic acid may be DNA or RNA. If RNA is used, a reverse transcriptase may be required to generate RNA from the DNA amplicon.

Figure 4:
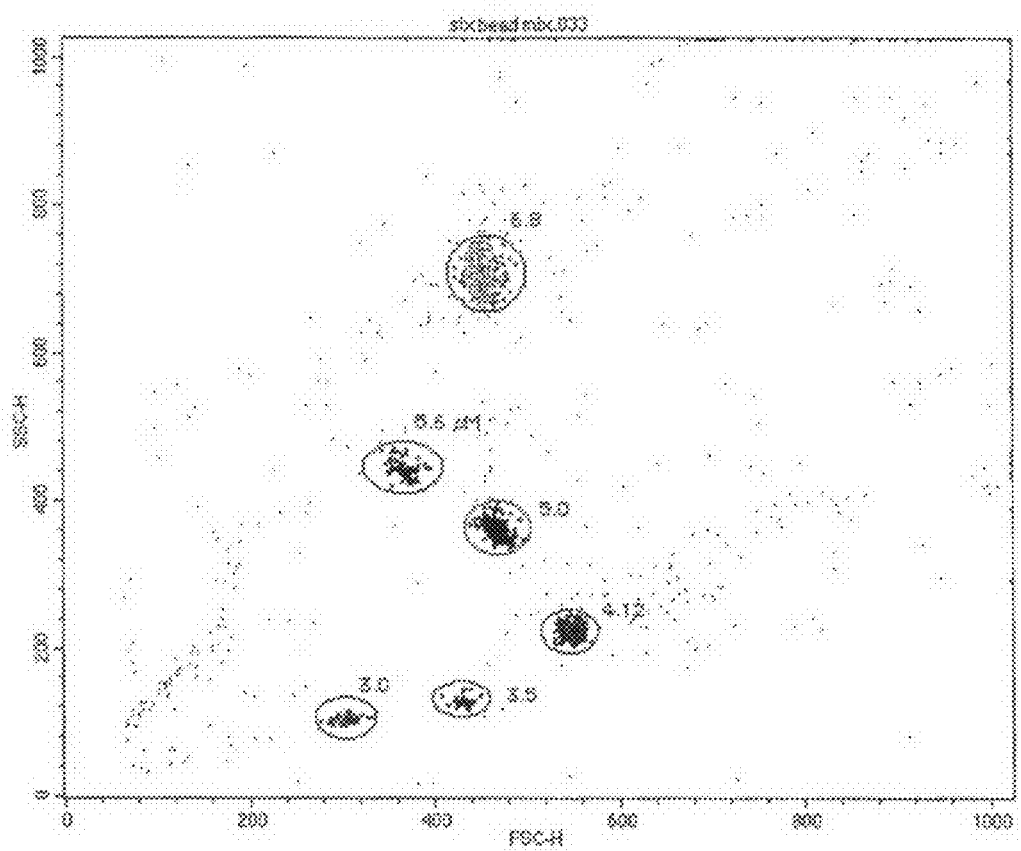
FIG. 4 is a graphical representation showing the differentiation of microspheres on the basis of size. Six clusters corresponding to microspheres comprising diameters of 3.0 µm, 3.5 µm, 4.1 µm, 5.0 µm, 5.6 µm and 6.8 µm are shown.

Each of the binding agents in the array is comprises a microsphere or bead with a distinct size and distinct intensity of fluorescent (TMR) label. Beads comprising diameters of 3.0 µm, 3.5 µm, 4.1 µm, 5.0 µm, 5.6 µm and 6.8 µm may be differentiated from each other using flow cytometry, as shown in FIG. 4.

Figure 5:
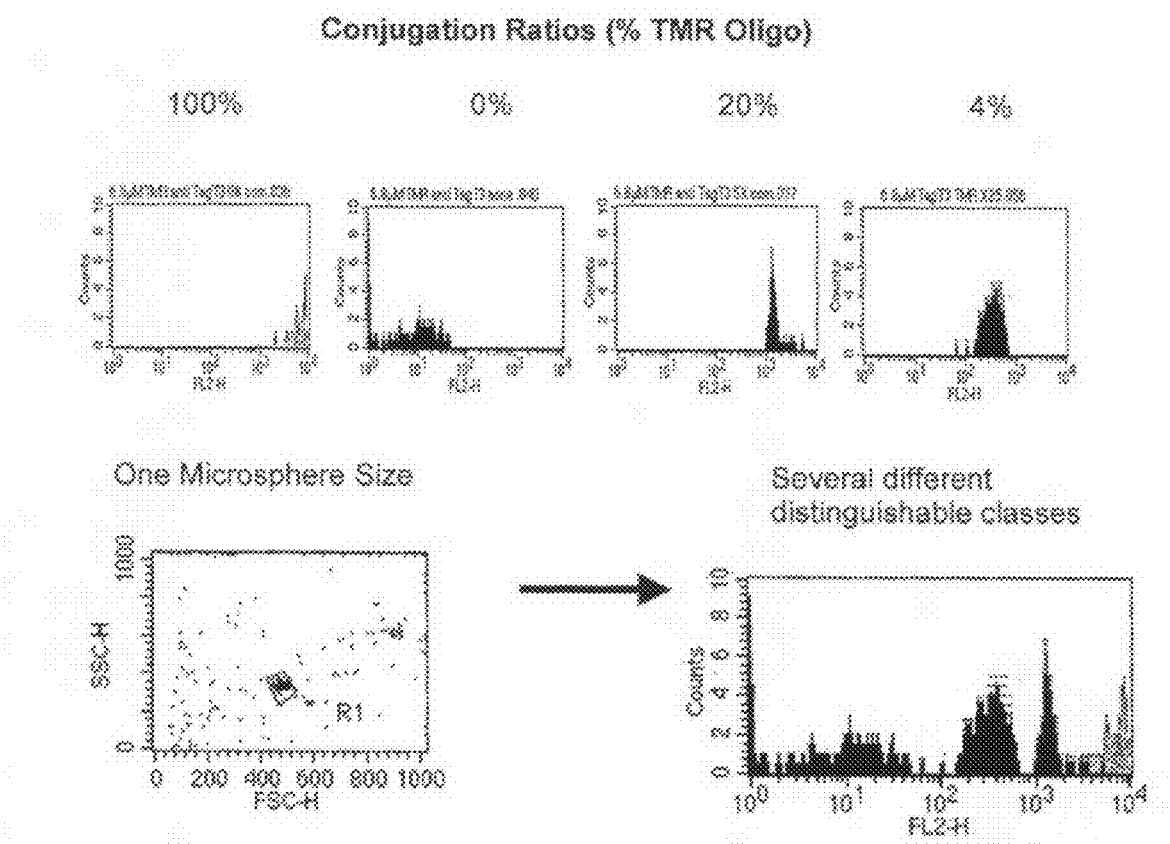
FIG. 5 is a graphical representation showing the differentiation of microspheres of the same size on the basis of fluorescent label intensity. TMR relative intensities of 0%, 4%, 20% and 100% could be clearly distinguished.

For each given size of microsphere, a fluorescent label (TMR) was incorporated at relative intensities of 0%, 4%, 20% and 100%. These label intensities could be clearly distinguished using flow cytometry as shown in FIG. 5. A machine for reading the intensities is shown in FIG. 1.

Figure 6:
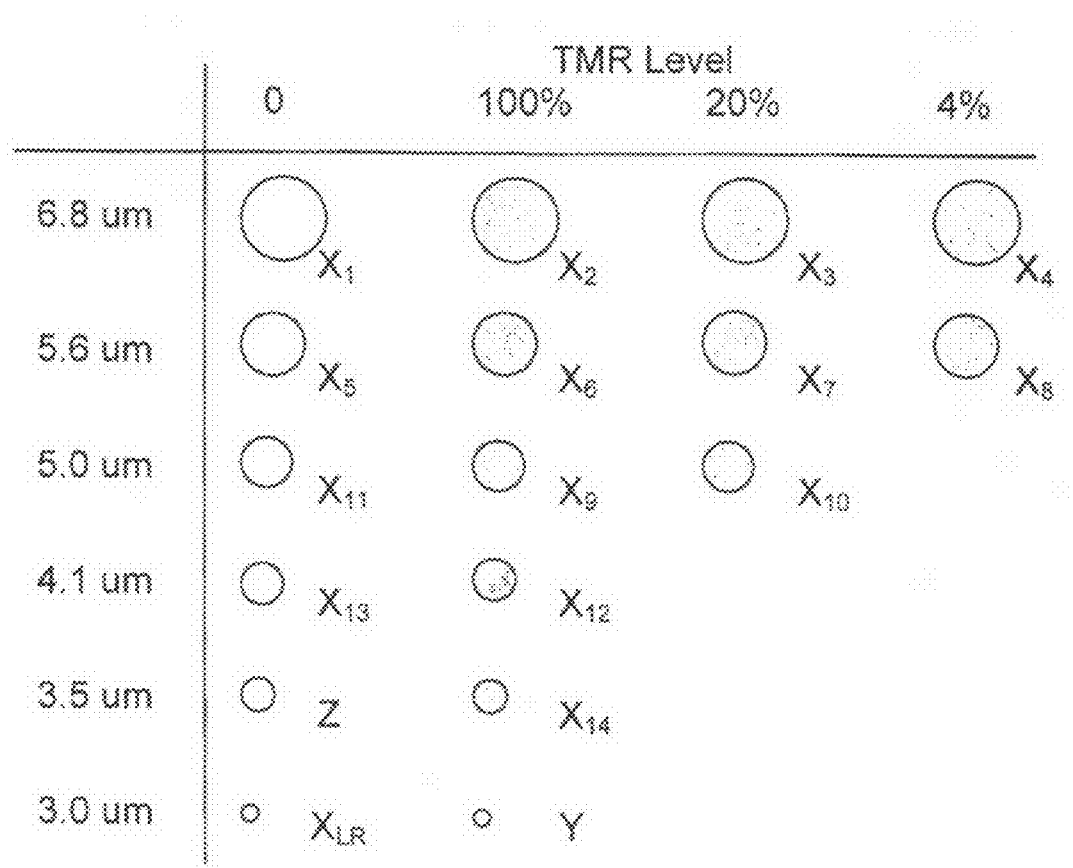
FIG. 6 is a schematic diagram showing each of the binding agents used in the array. The array comprises microspheres comprising diameters of 3.0 µm, 3.5 µm, 4.1 µm, 5.0 µm, 5.6 µm and 6.8 µm and fluorescent label signal intensities of 0%, 4%, 20% and 100%. In the case of the smaller bead sizes, ie. 3.0 µm, 3.5 µm and 4.1 µm, TMR intensities of 0% and 100% were used; for the 5.0 µm microspheres TMR intensities of 0%, 20% and 100% were used; and for the largest microspheres, the 5.6 µm and 6.8 µm diameter, all signal intensities were used.

FIG. 6 is a schematic diagram showing each of the binding agents used in the array. As can be seen, the array used microspheres comprising diameters of 3.0 µm, 3.5 µm, 4.1 µm, 5.0 µm, 5.6 µm and 6.8 µm and fluorescent label signal intensities of 0%, 4%, 20% and 100%. However in the case of the smaller bead sizes, fewer classes of signal intensity were used. FIG. 7 shows how each of these binding agents is distinguished on the basis of both size and fluorescent label intensity.

Figure 8:
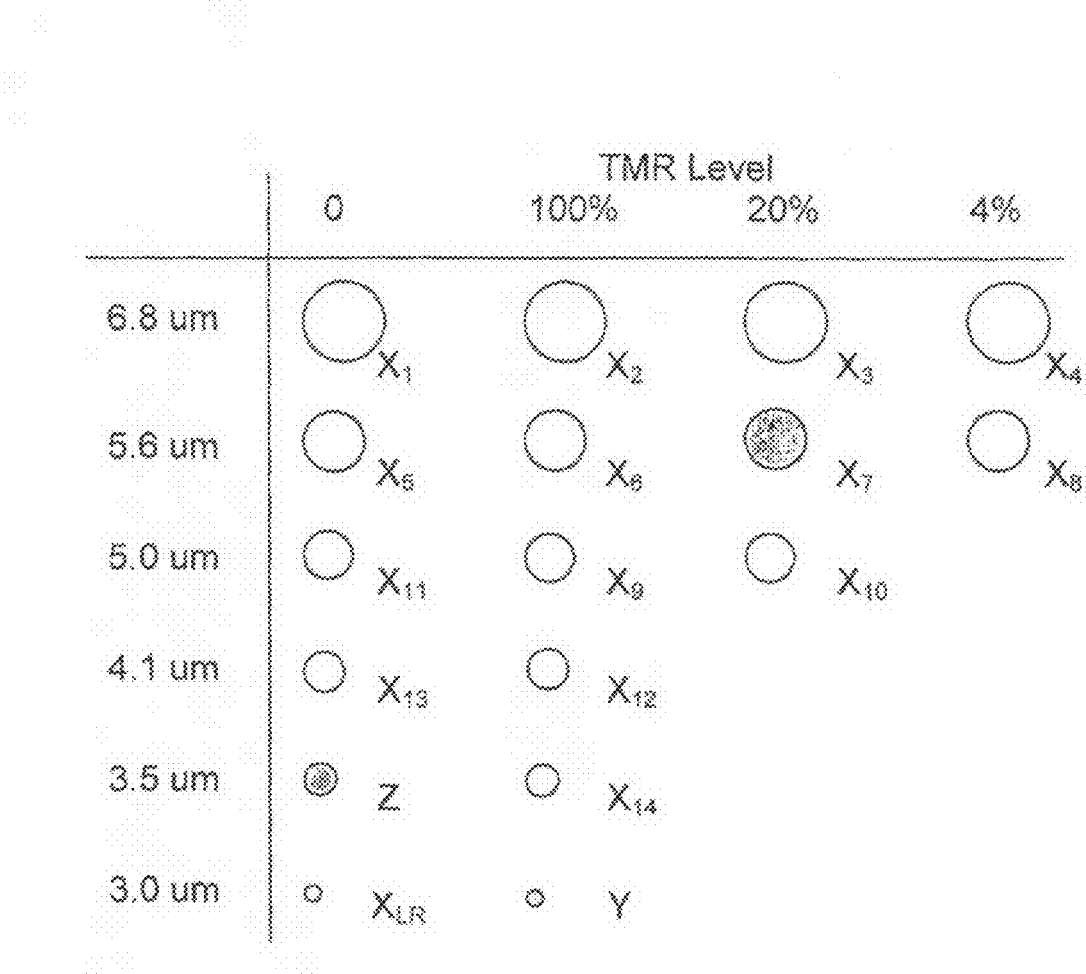
FIG. 8 is a graphical representation showing which of the binding agent array an amplicon has bound. The results show binding to the viral conserved sequence, Y, the human control sequence Z and the viral strain-specific sequence $X_{16}$.

FIG. 8 shows the association of bound amplicons with three specific binding agents in the array. In this figure, an amplicon is shown to bind to the human DNA control (Z), the viral conserved sequence (Y) and the viral variable sequence $X_7$, which is indicative of the presence of HPV strain 18 in the sample.

EXAMPLE 3

Comparison of the Multiplex Detection Method with Traditional HPV Diagnosis

Table 5, below, provides an overview comparing the multiplex HPV detection method of the present invention with the current histological method for HPV diagnosis.

EXAMPLE 4

Detection of HPV in Human Samples

FIGS. 10A through G provide examples where HPV is detected or is its absence noted in human samples.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any to or more of said steps or features.

BIBLIOGRAPHY

Bonner and Laskey, *Eur. J. Biochem.* 46:83, 1974

Chadwick et al., *J. Virol. Methods* 70:59-70, 1998

Chan and Fox, *Rev. Med. Microbiol.* 10:185-196, 1999

Compton, *Nature* 350:91-92, 1991

Demidov and Broude (Eds.), "*DNA Amplification: Current Technologies and Applications*", Horizon Bioscience, 2004

Gearhart et al., www.emedicine.com/MED/topic1037.htm, 2004

Guatelli et al., *Proc. Natl Acad. Sci. USA* 87:1874-1878, 1990

Hill, *J. Clin. Ligand Assay* 19:43-51, 1996

Kievits et al., *J. Virol. Methods* 35:273-286, 1991

Kuske et al., *Appl. Environ. Microbiol.* 64(7):2463-2472, 1998

Lizardi et al., *Biotechnology* 6:1197-1202, 1988

Lyamichev et al., *Nat. Biotechnol.* 17:292-296, 1999

Marmur and Doty, *J. Mol. Biol.* 5:109, 1962

Nelson and Krawetz, *Anal. Biochem.* 207(1):97-201, 1992

Pawlotsky et al., *J. Virol. Methods* 79:227-235, 1999

Ryan et al., *Mol. Diagn.* 4:135-144, 1999

Speel, *Histochem. Cell Biol.* 112:89-113, 1999

Todd et al., *J. AIDS Hum. Retrovirol.* 10:S35-S44, 1995

TABLE 5

| Comparison of HPV diagnostic methods | | | |
|---|---|---|---|
| HPV Diagnostic Method | Throughput | Report | Controls |
| Present Invention | 1600 per day, per instrument | all 13 "high risk" strains individually identified | internal control, positive control, human gDNA control |
| Histological based method | 350 per day | "high risk" class generally identified | no internal control, "low risk" positive control, "high reisk positive control |

What is claimed is:

1. A beadset for detecting a strain of HPV and/or for differentiating between two or more strains of HPV, wherein the beadset comprises a plurality of subsets of beads wherein:
   (a) the beads of each subset are homogenous with respect to size;
   (b) the beads within each subset are coupled to a nucleic acid capture probe which is capable of binding to a HPV strain-specific region of an HPV genome;
   (c) the capture probe on each bead is labeled with the same label with each subset of beads having a different fluorescent intensity to create a heterogeneous mixture of beads based on fluorescent intensity wherein the nucleic acid capture probe is selected from the group; and
   (d) at least two subsets of beads are mixed together to produce a beadset, wherein the subset identity and therefore the strain of HPV is identifiable by flow cytometry based on size, fluorescent intensity and sequence discrimination.

2. The beadset of claim 1 wherein the HPV strain is selected from group of strains consisting of 6, 11, 16, 18, 31, 33, 35, 39, 45, 51, 52, 56, 58, 59, 66 and 68.

3. The beadset of claim 2, wherein the HPV strain is selected from the group consisting of 6, 11, 31 and 33.

4. The beadset of claim 1, wherein the bead sizes are selected from the group consisting of 3.0 µm, 3.5 µm, 4.1 µm, 5.0 µm, 5.6 µm and 6.8 µm.

5. The beadset of claim 1, wherein the beads are labeled with a fluorochrome selected from the group consisting of hydroxycoumarin, aminocoumarin, methoxycoumarin, cascade blue, Lucifer yellow, Nitroben-zodiazole (NBD), Phycoerythrin (PE), Peridinin chlorphyll protein (PerCP), allophycocyanin, hoechst 33342, 4',6-diamidino-2-phenylindole (DAP1), SYTOX Blue, hoechst 33258, chromomycin A3, mithramycin, YOYO-1, SYTOX green, SYTOX orange, 7-Aminoactinomycin D (7-AAD), acridine orange, TOTO-1, To-PRO-1, thiazole orange, TOTO-3, TO-PRO-3, Laser Dye Styryl-751 (LDS 751), Alexa Fluor dyes including Alexa Fluoro-350, -430, -488, -532, -546, -555, -556, -594, -633, -647, -660, -680, -700 and -750; Boron-Dipyrromethene (BoDipy) dyes, including BoDipy 630/650 and BoDipy 650/665; Cyanine (CY) dyes, particularly Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4',5'-dichloro-2', 7'dimethoxyfluorescein (JOE); Oregon green dyes, including 488-X and 514; Rhodamine dyes, including X-Rhodamine, Lissamine Rhodamine B, Rhodamine Green, Rhodamine Red and ROX; Tetramethylrhodamine isothiocyanate (TRITC), Tetramethylrhodamine (TMR); Carboxytetramethylrhodamine (TAMRA); Tetrachlorofluorescein (TET); Red 6B, Fluor X, BODIPY-FL and Texas Red.

6. A method for preparing a bead set according to claim 1 for detecting one or more strains of HPV and/or for differentiating between two or more strains of HPV, the method comprising selecting a plurality of subsets of beads wherein:
   (a) the beads of each subset are homogenous with respect to size;
   (b) the beads within each subset are coupled to a nucleic acid capture probe which is capable of binding to a HPV strain-specific region of an HPV genome, wherein the nucleic acid capture probe is selected from the group consisting of SEQ ID NOs: 5 through 20;
   (c) the capture probe on each bead is labeled with the same label with each subset of beads having a different fluorescent intensity to create a heterogeneous mixture of beads based on fluorescent intensity; and
   (d) at least two subsets of beads are mixed together to produce a beadset, wherein the subset identity and therefore the strain of HPV is identifiable by flow cytometry based on size, fluorescent intensity and sequence discrimination.

7. The method of claim 6, wherein the HPV strain is selected from the group consisting of 6, 11, 16, 18, 31, 33, 35, 39, 45, 51, 52, 56, 58, 59, 66 and 68.

8. The method of claim 7, wherein the HPV strain is selected from the group consisting of strains 6, 11, 31 and 33.

9. The method of claim 6, wherein the bead sizes are selected from the group consisting of 3.0 µm, 3.5 µm, 4.1 µm, 5.0 µm, 5.6 µm and 6.8 µm.

10. The method of claim 6, wherein the beads are labeled with a fluorochrome selected from the group consisting of hydroxycoumarin, aminocoumarin, methoxycoumarin, cascade blue, Lucifer yellow, Nitroben-zodiazole (NBD), Phycoerythrin (PE), Peridinin chlorphyll protein (PerCP), allophycocyanin, hoechst 33342, 4',6-diamidino-2-phenylindole (DAP1), SYTOX Blue, hoechst 33258, chromomycin A3, mithramycin, YOYO-1, SYTOX green, SYTOX orange, 7-Aminoactinomycin D (7-AAD), acridine orange, TOTO-1, To-PRO-1, thiazole orange, TOTO-3, TO-PRO-3, Laser Dye Styryl-751 (LDS 751), Alexa Fluor dyes including Alexa Fluoro-350, -430, -488, -532, -546, -555, -556, -594, -633, -647, -660, -680, -700 and -750; Boron-Dipyrromethene (BoDipy) dyes, including BoDipy 630/650 and BoDipy 650/665; Cyanine (CY) dyes, particularly Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4',5'-dichloro-2', 7'dimethoxyfluorescein (JOE); Oregon green dyes, including 488-X and 514; Rhodamine dyes, including X-Rhodamine, Lissamine Rhodamine B, Rhodamine Green, Rhodamine Red and ROX; Tetramethylrhodamine isothiocyanate (TRITC), Tetramethylrhodamine (TMR); Carboxytetramethylrhodamine (TAMRA); Tetrachlorofluorescein (TET); Red 6B, Fluor X, BODIPY-FL and Texas Red.

11. A method for diagnosing HPV infection in a human subject, said method comprising:
   (i) obtaining a biological sample from the human subject which putatively comprises HPV;
   (ii) isolating nucleic acid from said sample;
   (iii) amplifying the nucleic acid from said sample using primers which generate an amplicon which is distinct for said analyte or a particular strain of said analyte;
   (iv) optionally amplifying a control nucleic acid sequence from the genomic DNA of the human subject;
   (v) optionally effecting labeling of the amplicon(s) recited at steps (iii) and/or (iv);
   (vi) hybridizing the labeled amplicon(s) to a beadset according to claim 1, wherein the beads of the beadset comprises a nucleic acid molecule having complementarity to a nucleotide sequence of HPV or a particular strain of HPV, bound or otherwise associated with a physiochemically distinguishable substrate; and
   (vii) determining to which of the reactants an amplicon has bound;
wherein the association of an amplicon with a particular reactant is indicative of HPV infection in the human subject.

12. The method of claim 11 wherein the HPV strain is selected from the group consisting of strains 6, 11, 16, 18, 31, 33, 35, 39, 45, 51, 52, 56, 58, 59, 66 and 68.

13. The method of claim 12, wherein the HPV strain is selected from the group consisting of 6, 11, 31 and 33.

14. The method of claim 11, wherein the bead sizes are selected from the group consisting of 3.0 µm, 3.5 µm, 4.1 µm, 5.0 µm, 5.6 µm and 6.8 µm.

15. The method of claim 11, wherein the beads are labeled with a fluorochrome selected from the group consisting of hydroxycoumarin, aminocoumarin, methoxycoumarin, cascade blue, Lucifer yellow, NBD, Phycoerythrin (PE), Peridinin chlorphyll protein (PerCP), allophycocyanin, hoechst 33342, 4',6-diamidino-2-phenylindole (DAP1), SYTOX Blue, hoechst 33258, chromomycin A3, mithramycin, YOYO-1, SYTOX green, SYTOX orange, 7-Aminoactinomycin D (7-AAD), acridine orange, TOTO-1, To-PRO-1, thiazole orange, TOTO-3, TO-PRO-3, Laser Dye Styryl-751 (LDS 751), Alexa Fluor dyes including Alexa Fluoro-350, -430, -488, -532, -546, -555, -556, -594, -633, -647, -660, -680, -700 and -750; Boron-Dipyrromethene (BoDipy) dyes, including BoDipy 630/650 and BoDipy 650/665; Cyanine (CY) dyes, particulary Cy2, Cy3, Cy3.5, Cy5, Cy 5.5 and Cy7; 6-FAM (Fluorescein); PE-Cy5, PE-Cy7, Fluorescein dT; Hexachlorofluorescein (Hex); 6-carboxy-4',5'-dichloro-2',7'-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; Tetramethylrhodamine isothiocyanate (TRITC), Tetramethylrhodamine (TMR); Carboxytetramethylrhodamine (TAMRA); Tetrachlorofluorescein (TET); Red 6B, Fluor X, BODIPY-FL and Texas Red.

\* \* \* \* \*

UNITED STATES PATENT AND TRADEMARK OFFICE
CERTIFICATE OF CORRECTION

| | | |
|---|---|---|
| PATENT NO. | : 7,901,883 B2 | Page 1 of 2 |
| APPLICATION NO. | : 11/721429 | |
| DATED | : March 8, 2011 | |
| INVENTOR(S) | : Poetter et al. | |

It is certified that error appears in the above-identified patent and that said Letters Patent is hereby corrected as shown below:

In column 2 (page 2 item 56) at line 29, Under Other Publications, change "Hepatitus" to --Hepatitis--.

In column 2 at line 55, Change "flurochromes" to --fluorochromes--.

In column 3 at line 42, Change "HPM" to --HPV--.

In column 4 at line 2, After "size;" delete "t".

In column 4 at line 24 (approx.), Change "flurochrome" to --fluorochrome--.

In column 4 at line 63 (approx.), Change "Carboxytetrametylrhodamine" to --Carboxytetramethylrhodamine--.

In column 4 at line 64 (approx.), Change "Teterachlorofluoresceine" to --Tetrachlorofluorescein--.

In column 6 at line 21, Change "stralns" to --strains--.

In column 7 at line 13, Change "flurochromes." to --fluorochromes.--.

In column 8 at line 17 (approx.), Change "flue" to --flu--.

In column 8 at line 18 (approx.), Change "HLTV-IV," to --HTLV-IV,--.

In column 8 at line 22, Change "coil" to --coli--.

In column 8 at line 24, Change "Nosicomial" to --Nosocomial--.

In column 8 at line 28, Change "Crytospiridium" to --Cryptosporidium--.

In column 8 at line 28, Change "anthacis" to --anthracis--.

In column 14 at line 7 (approx.), After "size;" delete "t".

In column 16 at line 43, Change "available" to --available.--.

In column 16 at line 50, Change "methoxyciumarin," to --methoxycoumarin,--.

In column 16 at line 51, Change "Phyccerythrin" to --Phycoerythrin--.

In column 16 at line 56, Change "Fluro-350," to --Fluoro-350,--.

In column 16 at line 56, Change "430, 488," to -- -430, -488,--.

Signed and Sealed this

Thirteenth Day of November, 2012

David J. Kappos
*Director of the United States Patent and Trademark Office*

CERTIFICATE OF CORRECTION (continued) Page 2 of 2

U.S. Pat. No. 7,901,883 B2

In column 17 at line 67, Change "formnamide" to --formamide--.

In column 19 at line 38, Change "10 m)" to --10 µm)--.

In column 27 at line 3, Change "µM," to --µm,--.

In column 27 at line 11, Change "futher" to --further--.

In column 29 (table 5) at line 8 (table 5), Change "reisk" to --risk--.

In column 30 at line 18 (approx.), Change "to" to --two--.

In column 40 at line 59, In Claim 1, change "group;" to --group consisting of SEQ ID NOs: 5 through 20;--.

In column 41 at line 9 (approx.), In Claim 5, change "chlorphyll" to --chlorophyll--.

In column 41 at line 59 (approx.), In Claim 10, change "chlorphyll" to --chlorophyll--.

In column 42 at line 45 (approx.), In Claim 15, change "chlorphyll" to --chlorophyll--.

In column 42 at line 54 (approx.), In Claim 15, change "particulary" to --particularly--.